(12) United States Patent
Bohlen et al.

(10) Patent No.: US 8,318,488 B1
(45) Date of Patent: Nov. 27, 2012

(54) ASSAY FOR DRUG DISCOVERY BASED ON IN VITRO DIFFERENTIATED CELLS

(75) Inventors: Heribert Bohlen, Köln (DE); Kristina Jönsson, Köln (DE); Andreas Ehlich, Mechernich (DE); Silke Schwengberg, Düren (DE)

(73) Assignee: Axiogenesis AG, Cologne (DE)

( * ) Notice: Subject to any disclaimer, the term of this patent is extended or adjusted under 35 U.S.C. 154(b) by 601 days.

(21) Appl. No.: 11/596,262

(22) PCT Filed: May 11, 2005

(86) PCT No.: PCT/EP2005/005087
§ 371 (c)(1),
(2), (4) Date: Aug. 29, 2007

(87) PCT Pub. No.: WO2005/108598
PCT Pub. Date: Nov. 17, 2005

(30) Foreign Application Priority Data

May 11, 2004 (EP) .................................. 04011214

(51) Int. Cl.
*C12N 5/00* (2006.01)
*C12N 5/02* (2006.01)

(52) U.S. Cl. ........................ 435/375; 435/377; 435/325

(58) Field of Classification Search ................. 435/375, 435/377, 325
See application file for complete search history.

(56) References Cited

U.S. PATENT DOCUMENTS

| | | | |
|---|---|---|---|
| 4,937,190 A | 6/1990 | Palmenberg | |
| 5,464,764 A | 11/1995 | Capecchi | |
| 5,733,727 A | 3/1998 | Field | |
| 5,900,361 A | 5/1999 | Klebe | |
| 5,928,943 A | 7/1999 | Franz | |
| 6,015,671 A | 1/2000 | Field | |
| 6,072,402 A | 6/2000 | Kniffin | |
| 6,080,576 A | 6/2000 | Zambrowicz | |
| 6,399,300 B1 | 6/2002 | Field | |
| RE37,978 E | 2/2003 | Field | |
| 6,581,161 B1 | 6/2003 | Byford | |
| 6,602,711 B1 | 8/2003 | Thomson | |
| 6,632,628 B1* | 10/2003 | Olson et al. ............... | 435/18 |
| 6,657,104 B1 | 12/2003 | Grant et al. | |
| 7,105,344 B2 | 9/2006 | Hescheler | |
| 2002/0092035 A1 | 7/2002 | Hescheler | |
| 2002/0160511 A1 | 10/2002 | Rambhatla et al. | |
| 2003/0022367 A1 | 1/2003 | Xu | |
| 2003/0102958 A1 | 6/2003 | Gudmundsson | |
| 2003/0108895 A1 | 6/2003 | Field et al. | |
| 2003/0119107 A1 | 6/2003 | Dang | |
| 2003/0170890 A1 | 9/2003 | Roenicke et al. | |
| 2004/0003424 A1 | 1/2004 | Olson et al. | |
| 2004/0096432 A1 | 5/2004 | Fleischmann et al. | |
| 2004/0117196 A1 | 6/2004 | Brockman | |
| 2005/0165612 A1 | 7/2005 | Van Rysselberghe | |
| 2006/0168665 A1 | 7/2006 | Hescheler | |
| 2007/0258948 A1 | 11/2007 | Kolossov et al. | |
| 2008/0019952 A1 | 1/2008 | Kolossov et al. | |

FOREIGN PATENT DOCUMENTS

| | | |
|---|---|---|
| DE | 299 439 | 5/1990 |
| DE | 19727962 | 7/1997 |
| DE | 198 43 234 A1 | 3/2000 |
| DE | 199 62154.3 | 7/2001 |
| EP | 1297851 | 4/2003 |
| EP | 1970446 | 9/2008 |
| EP | 1970446 A1 | 9/2008 |
| GB | 2 342 005 | 3/2000 |
| GB | 2 386 606 | 9/2003 |
| GB | 2 386 609 | 9/2003 |
| GB | 2386609 A | 9/2003 |
| GB | 2 387 501 | 10/2003 |
| JP | 10292688 | 11/1998 |
| JP | 11-502702 | 3/1999 |
| JP | 2002-508670 | 3/2002 |
| WO | WO94/24274 | 10/1994 |
| WO | WO95/07463 | 3/1995 |
| WO | WO95/14079 | 5/1995 |
| WO | WO95/21191 | 8/1995 |
| WO | WO96/16163 | 5/1996 |
| WO | WO96/27675 | 9/1996 |
| WO | WO96/29395 | 9/1996 |
| WO | WO98/36081 | 8/1998 |
| WO | WO98/54294 | 12/1998 |
| WO | WO99/01552 | 1/1999 |
| WO | WO 99/19471 A1 | 4/1999 |
| WO | WO01/62899 | 8/2001 |
| WO | WO 02/051987 A1 | 7/2002 |
| WO | WO 02/074925 A2 | 9/2002 |
| WO | WO 02/097128 | 12/2002 |

(Continued)

OTHER PUBLICATIONS

Yamashita et al., Histone deacetylase inhibitor trichostatin A induces cell-cycle arrest/apoptosis and hepatocyte differentiation in human hepatoma cells, Int J. Cancer, 103(5): 572-6, 2003.* Chen et al., Differentiation trapping screen in live culture for genes expressed in cardiovascular lineages, Dev Dyn. 229(2):319-27, Feb. 2004.*

Zweigerdt et al. Generation of confluent cardiomyocyte monolayers derived from embryonic stem cells in suspension: a cell source for new therapies and screening strategies, Cytotherapy 5(5):399-413, 2003.*

Sei et al., The alpha-adrenergic stimulation of atrial natriuretic factor expression in cardiac myocytes requires calcium influx, protein kinase C, and calmodulin-regulated pathways, J Biol Chem. 266(24):15910-6, 1991.*

Hescheler J., et al., "Embryonic stem cells: a model to study structural and functional properties in cardiomyogenesis," *Cardiovascular Research* 36:149-162, Elsevier Science (1997).

First Office Action for European Patent Application No. 05 740 642.3, dated Dec. 27, 2007.

(Continued)

*Primary Examiner* — Wu-Cheng Winston Shen

(74) *Attorney, Agent, or Firm* — Fanelli Haag & Kilger PLLC

(57) ABSTRACT

Provided are assay systems for determining the therapeutic or toxic effect of a putative drug based on assaying its activity in cells which have been differentiated in vitro from stem cells, and induced to display a phenotype that resembles a disease to be treated.

30 Claims, 8 Drawing Sheets

FOREIGN PATENT DOCUMENTS

| WO | WO 03/006950 A2 | 1/2003 |
|---|---|---|
| WO | WO03/010303 | 2/2003 |
| WO | WO 03/010303 A1 | 2/2003 |
| WO | WO 03/080816 A2 | 10/2003 |
| WO | WO2004/011603 | 2/2004 |
| WO | WO2004/003515 | 12/2004 |
| WO | WO2005/005621 | 1/2005 |
| WO | WO2005/005662 | 1/2005 |

OTHER PUBLICATIONS

International Search Report for International Application No. PCT/EP2005/005087, mailed on Jul. 14, 1997, European Patent Office, Netherlands.

U.S. Appl. No. 11/547,871, U.S. National Phase of PCT/EP2005/003662, Int'l Filing Date Apr. 7, 2005, § 371 Date Sep. 28, 2007.

U.S. Appl. No. 10/594,177, U.S. National Phase of PCT/EP2004/007529, Int'l Filing Date Jul. 8, 2004.

International Preliminary Report on Patentability for International Application No. PCT/EP2005/005087, completed on Apr. 18, 2006, European Patent Office, Munich, Germany.

Suzuki, et al., "Endothelin stimulates hypertrophy and contractility of neonatal rat cardiac myocytes in serum-free medium", FEBS Letters, vol. 268, No. 1, Jul. 1990, pp. 149-151.

Kolossov, et al., "Functional Characteristics of ES Cell-derived Cardiac Precursor Cells identified by Tissue-specific Expression of the Green Fluorescent Protein", The Journal of Cell Biology, vol. 143, No. 7, Dec. 28, 1998, pp. 2045-2056.

European Patent Office: "Notice of Opposition to European Patent No. 1745144", EP Patent Application No. 05740642.3, pp. 1-23, Aug. 19, 2011.

Fässler, R., et al., "Differentiation and integrity of cardiac muscle cells are impaired in the absence of β1 integrin," *J. Cell. Sci.* 109:2989-2999, The Company of Biologists Limited, United Kingdom (1996).

Weitzer, G., et al., "Cytoskeletal Control of Myogenesis: A Desmin Null Mutation Blocks the Myogenic Pathway during Embryonic Stem Cell Differentiation," *Dev. Biol.* 172:422-439, Academic Press, Inc., United States (1995).

Wobus, A., et al., "Retinoic Acid Accelerates Embryonic Stem Cell-Derived Cardiac Differentiation and Enhances Development of Ventricular Cardiomyocytes, "*J. Mol. Cell Cardiol.* 29:1525-1539, Academic Press, Ltd., United States (1997).

Unverified English language abstract of DE 19843234 A1, Wobus, A., et al., Esp@ce Database, European Patent Office, 1 page. (2000).

White, et al., "Cardiac physiology at the cellular level: use of cultured HL-1 cardiomyocytes for studies of cardiac muscle cell structure and function" Am J Physiol Heart Circ Physiol, 286: H823-H829, 2004.

Molkentin, et al., "A Calcineurin-Dependent Transcriptional Pathway for Cardiac Hypertrophy" Cell, vol. 93, Apr. 17, 1998, pp. 215-228.

Response to Communication pursuant to Rule 79(1) EPC dated Sep. 26, 2011, pp. 1-14.

Sabbah, "Biologic Rationale for the Use of Beta-Blockers in the Treatment of Heart Failure", Heart Failure Reviews, 9, 91-97, 2004.

Sugden, "Ras, Akt, and Mechanotransduction in the Cardiac Myocyte", National Heart and Lung Institute Division (Cardiac Medicine Section), Faculty of Medcine. Imperial College of Science, Technology and Medicine, London UK, Downloaded from circres.ahajournals.org on Oct. 28, 2010.

Földes, et al., "Modulation of human embryonic stem cell-derived cardiomyocyte growth: A testbed for studying human cardiac hypertrophy?", Journal of Molecular Cardiology, 50, 367-376, 2011.

Carvajal-Vergara, et al., "Patient-specific induced pluripotent stem-cell-derived models of LEOPARD syndrome", Nature, vol. 465, 808-814, Jun. 2010.

Takemura, et al., "Phenotype alteration of failing myocardium", Nippon Rinsho, 61(5):731-738, May 2003 (ABSTRACT) Article in Japanese.

Yamazaki, T., et al., "Molecular Mechanism of Cardiac Cellular Hypertrophy by Mechanical Stress," J. Mol. Cell. Cardiol. 27:133-140 (1995) [Abstract #0536].

Sachinidis, A., et al., "Cardiac specifc differentiation of mouse embryonic stem cells," Cardiovascular Research 58:278-291, May 2003.

Huang, W-Y, et al., "Transgenic expression of green fluorescence protein can cause dilated cardiomyopathy," Nat. Med. 6:482-484, Nature American Inc. (May 2000).

EP 05740642—Papers filed in EP opposition proceedings in counterpart European application.

* cited by examiner

ASSAY FOR DRUG DISCOVERY BASED ON IN VITRO DIFFERENTIATED CELLS

SEQUENCE LISTING

The instant application contains a Sequence Listing which has been submitted in ASCII format via EFS-Web and is hereby incorporated by reference in its entirety. Said ASCII copy, created on Sep. 6, 2012, is named 0066_0002_US1_Sequence_Listing and is 5,146 bytes in size.

FIELD OF THE INVENTION

The present invention relates to the technical field of cell-based assays for identifying and/or obtaining a drug for the amelioration or treatment of a disease or for determining the toxicity of a given compound. In particular, the present invention relates to a method for identifying and/or obtaining a drug for the amelioration or treatment of a disease or for determining the toxicity of a compound comprising contacting a test sample comprising an in vitro differentiated cell with a test substance to be screened, wherein said cell is induced to display a predefined diseased phenotype which substantially corresponds to a phenotype of a diseased cell, tissue or organ; and determining a responsive change of the phenotype in said test sample, wherein a responsive change preventing or delaying the onset or the progression of the diseased phenotype is indicative for a useful drug, and enhancing the onset or progression the diseased phenotype is indicative for the toxicity of the compound. The method of the present invention is preferably employed with embryonic stem cells and can be generally applied for the identification of protective effects of any promising therapeutic compound, and also for determining potential side effects a given compound may have for a subject suffering from a particular disease. The assay of the present invention is particularly suited for screening the ability of a substance to ameliorate cardiomyopathy. Furthermore, the present invention concerns kits and an apparatus for performing the cell-based assay of the invention and for analyzing the results so obtained.

BACKGROUND OF THE INVENTION

Heart disease is one of the most serious health concerns in the western world. It is estimated that 61 million Americans (nearly 1 in 5 men and women) have one or more types of cardiovascular disease (National Health and Nutrition Examination Survey III, 1988-1994, Center of Disease Control and the American Heart Association). Widespread conditions include coronary heart disease (12.4 million), congenital cardiovascular defects (1 million), and congestive heart failure (4.7 million). A central challenge for research in regenerative medicine is to identify and develop drugs that can help reconstitute cardiac function in these conditions.

The development of new drugs is hampered by the lack of suitable cell-based in vitro systems that resemble a diseased tissue, for example myopathic cardiac cells. A variety of attempts to obtain immortalized cardiac myocytes are described in Sen et al., J. Biol. Chem. 263 (1988), 19132-19136; Gartside and Hauschka in "The Development and Regenerative Potential of Cardiac Muscle", eds. Oberpriller et al., Harwood, N.Y., 1991, 7941-7948; Jaffredo et al., Exp. Cell. Res. 192 (1991), 481-491; Wang et al., In Vitro Cell Dev. Biol. 27 (1991), 63-74; Katz et al., Am. J. Physiol. 262 (1992), 1867-1876); Engelmann et al., J. Mol. Cell. Cardiol. 25 (1993), 197-213; Borisov and Claycomb, Ann. NY Acad. Sci. 752 (1995), 80-91; Jahn et al., J. Cell Sci. 109 (1996), 397-407. However, the cardiac phenotype of the cells so obtained either is not stable, or the cells loose their ability to proliferate. Furthermore, a cell line of murine immortalized, atrial cardiomyocytes has been described, which maintains features of differentiation and capability of proliferation over a longer period of time (Claycomb et al., Proc. Natl. Acad. Sci. USA 95 (1998), 2979-2984).

As an in vitro heart disease model system based on non-transformed cardiomyocytes often preparations of heart cells isolated from mouse or rat are used; see Chlopcikova et al., Biomed. Pap. Med. Fac. Univ. Palacky Olomouc Czech. Repub. 145 (2001), 49-55. These cells maintain their differentiated phenotype for a few days only. Furthermore, these primary cultures are not homogeneous but contain different cell types and vary for each preparation. A particular problem consists in the contamination of the cardiomyocytes by other cell types present in the heart, in particular fibroblasts, which in contrast to resting cardiomyocytes strongly proliferate and cannot entirely be eliminated from the culture. Some receptors expressed by cardiomyocytes as well as by non-cardiomyocyte cells and cardiomyocytes secrete molecules which interact with receptors from non-cardiomyocytes, as well as vice versa non-cardiomyocytes secrete molecules which bind to receptors from cardiomyocytes.

Accordingly, in view of the quite laborious preparation of cells of tissue or organs, which could serve as model system for a disease phenotype in vitro, transgenic animal models are still used such as the transgenic animal model of heart failure described in international application WO97/36477 or for human cardiomyopathy described in German patent application No. 198 15 128. Recently, a transgenic animal model to produce cardiac hypertrophy in transgenic mice has been described in U.S. Pat. No. 6,657,104.

However, these test procedures have the disadvantage that they require the use of a large number of live mammals, in particular rats and mice, and obviously are not amenable to high throughput screening.

Thus, there is a need for cell-based in vitro assay systems that can be easily performed and give reliable results. The solution to said technical problem is achieved by providing the embodiments characterized in the claims, and described further below.

SUMMARY OF THE INVENTION

The present invention is directed to a method for identifying and/or obtaining a drug for the amelioration or treatment of a disease or for determining the toxicity of a compound comprising contacting a test sample comprising an in vitro differentiated cell with a test substance to be screened, wherein said cell is induced to display a predefined diseased phenotype which substantially corresponds to a phenotype of a diseased cell, tissue or organ; and determining a responsive change of the phenotype in said test sample, wherein a responsive change preventing or delaying the onset or the progression of the diseased phenotype is indicative for a useful drug, and enhancing the onset or progression the diseased phenotype is indicative for the toxicity of the compound.

Furthermore, the present invention relates to a method for screening a substance for the ability to ameliorate cardiomyopathy comprising contacting a test sample comprising an in vitro differentiated cardiomyocyte with a test substance prior, during or after said cell is induced to display a predefined diseased phenotype which substantially corresponds to a phenotype of a diseased cell, tissue or organ; measuring a cardiomyopathic parameter in the cardiomyocyte; and comparing the measurement so obtained to that of a cardiomyocyte not subjected to the substance; wherein the measurement of the cardiomyopathic parameter in the cardiomyocytes is consistent with a reduction in cardiac hypertrophy.

The present invention also concerns a kit or composition useful for conducting the in vitro differentiated cell-based assay of the present invention, containing a multi- or pluripotent cell, an in vitro differentiated cell, a physiologically active agent, and optionally culture medium, recombinant nucleic acid molecules, and/or standard compounds.

It is an object of the present invention to provide a method of identifying and/or obtaining a gene or gene product involved in a disease as a drug target comprising expression profiling of an in vitro differentiated cell before and after induction of a diseased phenotype, wherein the differential expression of a gene or gene product is indicative for a potential drug target, and optionally comprising cloning the identified gene or a corresponding cDNA or fragment thereof.

It is another object of the present invention to provide a method of validating a potential drug target comprising altering the expression of a target gene and/or activity of the target gene product in an in vitro differentiated cell prior, during or after said cell is induced to display a predefined diseased phenotype which substantially corresponds to a phenotype of a diseased cell, tissue or organ; and determining a responsive change of the phenotype of said cell, wherein a responsive change preventing or delaying the onset or the progression of the diseased phenotype is indicative for a drug target to be activated, and enhancing the onset or progression the diseased phenotype is indicative for a drug target to be inhibited for the treatment of the disease.

According to another aspect, the invention relates to the use of an in vitro differentiated cell which is induced to display a predefined diseased phenotype in target validation, drug discovery or pharmacokinetic or pharmacological profiling.

In yet another embodiment of the invention a method of conducting a target discovery business comprising providing a cell-based assay of the invention; and/or conducting toxicity and/or therapeutic profiling of a compound in such assay; and licensing, to a third party, the rights for further drug development and/or sales for a drug identified in an assay of the present invention and/or providing the information on the profile so obtained is provided. Other embodiments of the invention will be apparent from the description that follows.

DEFINITIONS

Figure 1A:
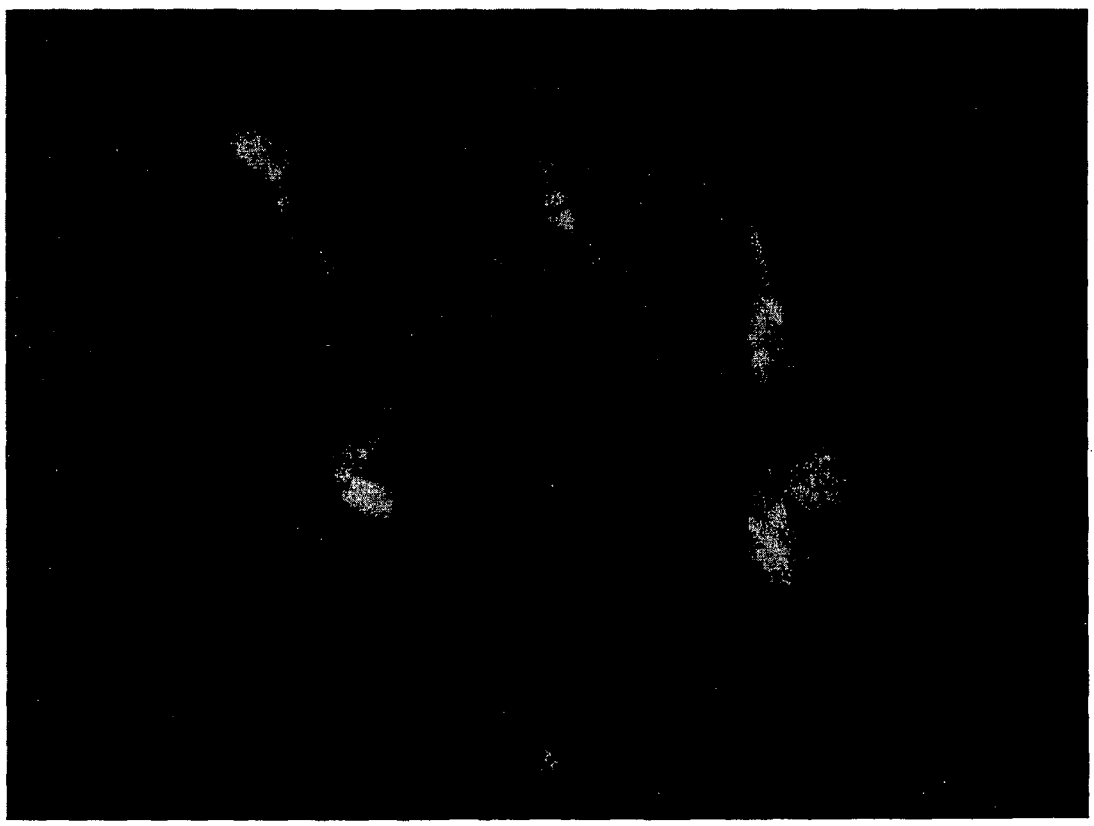
FIG. 1: ES cell-derived cardiomyocytes increase in size upon stimulation by endothelin-1 and phenylephrine. GFP-expressing cardiomyocytes were cultured on inactive embryonic mouse fibroblasts and serum-starved for 24 h. Subsequently, cultures were stimulated for 24 h by phenylephrine (A; 100 µM) or endothelin-1 (B; 100 nM). C; untreated cells.

For the purposes of this description, the term "stem cell" can refer to either stem cell or germ cell, for example embryonic stem (ES) and germ (EG) cell, respectively, but also including adult stem cells. Minimally, a stem cell has the ability to proliferate and form cells of more than one different phenotype, and is also capable of self renewal-either as part of the same culture, or when cultured under different conditions. Embryonic stem cells are also typically telomerase positive and OCT-4 positive. Telomerase activity can be determined using TRAP activity assay (Kim et al., Science 266 (1997), 2011), using a commercially available kit (TRAPeze® XK Telomerase Detection Kit, Cat. s7707; Intergen Co., Purchase N.Y.; or TeloTAGGG™ Telomerase PCR ELISAplus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

In accordance with the present invention, the term embryonic stem (ES) cell includes any multi- or pluripotent stem cell-derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice. "Embryonic germ cells" or "EG cells" are cells derived from primordial germ cells. The term "embryonic germ cell" is used to describe cells of the present invention that exhibit an embryonic pluripotent cell phenotype. The terms "human embryonic germ cell (EG)" or "embryonic germ cell" can be used interchangeably herein to describe mammalian, preferably human cells, or cell lines thereof, of the present invention that exhibit a pluripotent embryonic stem cell phenotype as defined herein. Thus, EG cells are capable of differentiation into cells of ectodermal, endodermal, and mesodermal germ layers. EG cells can also be characterized by the presence or absence of markers associated with specific epitope sites identified by the binding of particular antibodies and the absence of certain markers as identified by the lack of binding of certain antibodies.

"Pluripotent" refers to cells that retain the developmental potential to differentiate into a wide range of cell lineages including the germ line. The terms "embryonic stem cell phenotype" and "embryonic stem-like cell" also are used interchangeably herein to describe cells that are undifferentiated and thus are pluripotent cells and that preferably are capable of being visually distinguished from other adult cells of the same animal.

Included in the definition of ES cells are embryonic cells of various types, exemplified by human embryonic stem cells, described by Thomson et al. (Science 282 (1998), 1145); embryonic stem cells from other primates, such as Rhesus stem cells (Thomson et al., Proc. Natl. Acad. Sci. USA 92 (1995), 7844), marmoset stem cells (Thomson et al., Biol. Reprod. 55 (1996), 254) and human embryonic germ (hEG) cells (Shamblott et al., Proc. Natl. Acad. Sci. USA 95 (1998), 13726). Other types of pluripotent cells are also included in the term. Any cells of mammal origin that are capable of producing progeny that are derivatives of all three germinal layers are included, regardless of whether they were derived from embryonic tissue, fetal tissue, or other sources. The stem cells employed in accordance with the present invention that are preferably (but not always necessarily) karyotypically normal. However, it is preferred not to use ES cells that are derived from a malignant source.

"Feeder cells" or "feeders" are terms used to describe cells of one type that are co-cultured with cells of another type, to provide an environment in which the cells of the second type can grow. The feeder cells are optionally from a different species as the cells they are supporting.

For example, certain types of ES cells can be supported by primary mouse embryonic fibroblasts, immortalized mouse embryonic fibroblasts (such as murine STO cells, e.g., Martin and Evans, Proc. Natl. Acad. Sci. USA 72 (1975), 1441-1445), or human fibroblast-like cells differentiated from human ES cells, as described later in this disclosure. The term "STO cell" refers to embryonic fibroblast mouse cells such as are commercially available and include those deposited as ATCC CRL 1503.

The term "embryoid bodies" (EBs) is a term of art synonymous with "aggregate bodies". The terms refer to aggregates of differentiated and undifferentiated cells that appear when ES cells overgrow in monolayer cultures, or are maintained in suspension cultures. Embryoid bodies are a mixture of different cell types, typically from several germ layers, distinguishable by morphological criteria; see also infra. As used herein, "embryoid body", "EB" or "EB cells" typically refers to a morphological structure comprised of a population of cells, the majority of which are derived from embryonic stem (ES) cells that have undergone differentiation. Under culture conditions suitable for EB formation (e.g., the removal of Leukemia inhibitory factor or other, similar blocking factors), ES cells proliferate and form small mass of cells that begin to differentiate. In the first phase of differentiation, usually corresponding to about days 1-4 of differentiation for humans, the small mass of cells forms a layer of endodermal cells on the outer layer, and is considered a "simple embryoid body". In the second phase, usually corresponding to about days 3-20 post-differentiation for humans, "complex embryoid bodies" are formed, which are characterized by extensive differentiation of ectodermal and mesodermal cells and derivative tissues. As used herein, the term "embryoid body" or "EB" encompasses both simple and complex embryoid bodies unless otherwise required by context. The determination of when embryoid bodies have formed in a culture of ES cells is routinely made by persons of skill in the art by, for example, visual inspection of the morphology. Floating masses of about 20 cells or more are considered to be embryoid bodies; see. e.g., Schmitt et al., Genes Dev. 5 (1991), 728-740; Doetschman et al., J. Embryol. Exp. Morph. 87 (1985), 27-45. It is also understood that the term "embryoid body", "EB", or "EB cells" as used herein encompasses a population of cells, the majority of which being pluripotent cells capable of developing into different cellular lineages when cultured under appropriate conditions. As used herein, the term also refers to equivalent structures derived from primordial germ cells, which are primitive cells extracted from embryonic gonadal regions; see, e.g., Shamblott, et al. (1998), supra. Primordial germ cells, sometimes also referred to in the art as EG cells or embryonic germ cells, when treated with appropriate factors form pluripotent ES cells from which embryoid bodies can be derived; see, e.g., U.S. Pat. No. 5,670,372; Shamblott, et al., supra.

The terms "polynucleotide" and "nucleic acid molecule" refer to a polymer of nucleotides of any length. Included are genes and gene fragments, mRNA, tRNA, rRNA, ribozymes, cDNA, recombinant polynucleotides, branched polynucleotides, plasmids, vectors, isolated DNA and RNA, nucleic acid probes, and primers. As used in this disclosure, the term polynucleotides refer interchangeably to double- and single-stranded molecules. Unless otherwise specified or required, any embodiment of the invention that is a polynucleotide encompasses both a double-stranded form, and each of the two complementary single-stranded forms known or predicted to make up the double-stranded form. Included are nucleic acid analogs such as phosphoramidates and thiophosphoramidates.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

A "regulatory sequence" or "control sequence" is a nucleotide sequence involved in an interaction of molecules that contributes to the functional regulation of a polynucleotide, such as replication, duplication, transcription, splicing, polyadenylation, translation, or degradation of the polynucleotide. Transcriptional control elements include promoters, enhancers, and repressors.

Particular gene sequences referred to as promoters, like the "αMHC" or "collagen" promoter, are polynucleotide sequences derived from the gene referred to that promote transcription of an operatively linked gene expression product. It is recognized that various portions of the upstream and intron untranslated gene sequence may in some instances contribute to promoter activity, and that all or any subset of these portions may be present in the genetically engineered construct referred to. The promoter may be based on the gene sequence of any species having the gene, unless explicitly restricted, and may incorporate any additions, substitutions or deletions desirable, as long as the ability to promote transcription in the target tissue. Genetic constructs designed for treatment of humans typically comprise a segment that is at least 90% identical to a promoter sequence of a human gene.

According to the present invention, the term "cell- and/or development-dependent promoter" is intended to mean a promoter which displays its promoter activity only in particular cell types and/or only in particular stages of cellular development, both in cell cultures (embryoid bodies) and in transgenic non-human mammals derived from the ES cells according to the invention. In addition, any other known cell-specific promoter can be employed, e.g. for nerve cells, heart cells, neurons, glia cells, hematopoietic cells, endothelial cells, smooth muscle cells, skeletal muscle cells, cartilage cells, fibroblasts and epithelial cells.

Genetic elements are said to be "operatively linked" if they are in a structural relationship permitting them to operate in a manner according to their expected function. For instance, if a promoter helps initiate transcription of the coding sequence, the coding sequence can be referred to as operatively linked to (or under control of) the promoter. There may be intervening sequence between the promoter and coding region so long as this functional relationship is maintained.

In the context of encoding sequences, promoters, and other genetic elements, the term "heterologous" indicates that the element is derived from a genotypically distinct entity from that of the rest of the entity to which it is being compared. For example, a promoter or gene introduced by genetic engineering techniques into an animal of a different species is said to be a heterologous polynucleotide. An "endogenous" genetic element is an element that is in the same place in the chromosome where it occurs in nature, although other elements may be artificially introduced into a neighboring position.

The terms "polypeptide", "peptide" and "protein" are used interchangeably in this disclosure to refer to polymers of amino acids of any length. The polymer may comprise modified amino acids, it may be linear or branched, and it may be interrupted by non-amino acids.

If not stated otherwise the terms "compound", "substance" and "(chemical) composition" are used interchangeably herein and include but are not limited to therapeutic agents (or potential therapeutic agents), food additives and nutraceuticals, agents of known toxicities such as neurotoxins, hepatic toxins, toxins of hematopoietic cells, myotoxins, carcinogens, teratogens, or toxins to one or more reproductive organs. The chemical compositions can further be agricultural chemicals, such as pesticides, fungicides, nematicides, and fertilizers, cosmetics, including so-called "cosmeceuticals", industrial wastes or by-products, or environmental contaminants. They can also be animal therapeutics or potential animal therapeutics. Industrial products that can be tested with the methods of the present invention include bleaches, toilet, blocks, washing-up liquids, soap powders and liquids, fabric conditioners, window, oven, floor, bathroom, kitchen and carpet cleaners, dishwater detergents and rinse aids, watersoftening agents, descalers, stain removers, polishes, oil products, paints, paint removers, glues, solvents, varnishes, air fresheners, moth balls and insecticides.

New ingredients for household products are constantly being developed and needed to be tested. For example, in recent years new enzymes (to digest stains) and "optical brighteners" (which make washing appear whiter) have been developed for use in washing powders and liquids. New surfactants (which cut through grease to remove ingrained dirt) and chemical "builders" (which act as water softeners and enable surfactants to work more effectively) have been developed for use in washing powders and liquids, washing-up liquids and various cleaning agents. But also medical materials have to be tested, for example dental materials such as new filling polymers, metal alloys, and bioactive ceramic. Furthermore, chemical compositions of any part of a device, such as catheters, electrodes, adhesives, paste, gel or cream may be tested with the method of the present invention in different concentrations and with different ingredients and impurities present.

Compounds to be screened may also be obtained from diversity libraries, such as random or combinatorial peptide or non-peptide libraries. Many libraries are known in the art that can be used, e.g., chemically synthesized libraries, recombinant (e.g., phage display libraries), and in vitro translation-based libraries.

Examples of chemically synthesized libraries are described in Fodor et al., Science 251 (1991), 767-773; Houghten et al., Nature 354 (1991), 84-86; Lam et al., Nature 354 (1991), 82-84; Medynski, Bio/Technology 12 (1994), 709-710; Gallop et al., J. Medicinal Chemistry 37(9), (1994), 1233-1251; Ohmeyer et al., Proc. Natl. Acad. Sci. USA 90 (1993), 10922-10926; Erb et al., Proc. Natl. Acad. Sci. USA 91 (1994), 11422-11426; Houghten et al., Biotechniques 13 (1992), 412; Jayawickreme et al., Proc. Natl. Acad. Sci. USA 91 (1994), 1614-1618; Salmon et al., Proc. Natl. Acad. Sci. USA 90 (1993), 11708-11712; international application WO93/20242; and Brenner and Lerner, Proc. Natl. Acad. Sci. USA 89 (1992), 5381-5383.

Examples of phage display libraries are described in Scott and Smith, Science 249 (1990), 386-390; Devlin et al., Science 249 (1990), 404-406; Christian et al., J. Mol. Biol. 227 (1992), 711-718; Lenstra, J. Immunol. Meth. 152 (1992), 149-157; Kay et al., Gene 128 (1993), 59-65; and international application WO94/18318.

In vitro translation-based libraries include but are not limited to those described in international application WO91/05058; and Mattheakis et al., Proc. Natl. Acad. Sci. USA 91 (1994), 9022-9026.

By way of examples of non-peptide libraries, a benzodiazepine library (see e.g., Bunin et al., Proc. Natl. Acad. Sci. USA 91 (1994), 4708-4712) can be adapted for use. Peptide libraries (Simon et al., Proc. Natl. Acad. Sci. USA 89 (1992), 9367-9371) can also be used. Another example of a library that can be used, in which the amide functionalities in peptides have been permethylated to generate a chemically transformed combinatorial library, is described by Ostresh et al., Proc. Natl. Acad. Sci. USA 91 (1994), 11138-11142.

Screening the libraries can be accomplished by any of a variety of commonly known methods; see, e.g., the following references, which disclose screening of peptide libraries: Parmley and Smith, Adv. Exp. Med. Biol. 251 (1989), 215-218; Scott and Smith, Science 249 (1990), 386-390; Fowlkes et al., BioTechniques 13 (1992), 422-427; Oldenburg et al., Proc. Natl. Acad. Sci. USA 89 (1992), 5393-5397; Yu et al., Cell 76 (1994), 933-945; Staudt et al., Science 241 (1988), 577-580; Bock et al., Nature 355 (1992), 564-566; Tuerk et al., Proc. Natl. Acad. Sci. USA 89 (1992), 6988-6992; Ellington et al., Nature 355 (1992), 850-852; U.S. Pat. No. 5,096,815, U.S. Pat. No. 5,223,409, and U.S. Pat. No. 5,198,346; Rebar and Pabo, Science 263 (1993), 671-673; and international application WO94/18318.

As used herein, "profile" or "profiling" of a chemical composition or compound refers to a pattern of alterations in gene or protein expression, or both, or physiological properties in an ES cell, embryoid body, tissue, etc. contacted by the chemical composition compared to a like cell, embryoid body or tissue in contact only with culture medium.

Differentiation is the process whereby relatively unspecialized cells (e.g., stem cells) acquire specialized structural and/or functional features characteristic of mature cells. Similarly, "differentiate" refers to this process. Typically, during differentiation, cellular structure alters and tissue-specific proteins appear.

The term "diseased" is used herein to denote a cell, tissue or organ caused by or altered by or manifesting a disease or pathology. For example, a "diseased cardiomyocyte" may be a "myopathic" cardiomyocyte, i.e. a cardiomyocyte suffering from cardiomyopathy. The term "diseased phenotype" is used herein to indicate that a cell which otherwise would be regarded as a diseased cell is not originally derived from a diseased tissue or organ but has been induced in vitro to display substantially the same phenotype as said diseased cell. The term "pathologic" or "pathological" may be used interchangeably with the term "diseased".

General Techniques

For further elaboration of general techniques useful in the practice of this invention, the practitioner can refer to standard textbooks and reviews in cell biology, tissue culture, embryology, and cardiophysiology.

With respect to tissue culture and embryonic stem cells, reference can be made to Teratocarcinomas and embryonic stem cells: A practical approach (Robertson, ed., IRL Press Ltd. 1987); Guide to Techniques in Mouse Development (Wasserman et al. eds., Academic Press 1993); Embryonic Stem Cell Differentiation in Vitro (Wiles, Meth. Enzymol. 225 (1993), 900); Properties and uses of Embryonic Stem Cells: Prospects for Application to Human Biology and Gene Therapy (Rathjen et al., Reprod. Fertil. Dev. 10 (1998), 31). With respect to the culture of heart cells, standard references include The Heart Cell in Culture (Pinson ed., CRC Press 1987); Isolated Adult Cardiomyocytes (Vols. I & II, Piper & Isenberg eds., CRC Press 1989); and Heart Development (Harvey & Rosenthal, Academic Press 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as Bio-Rad, Stratagene, Invitrogen, Sigma-Aldrich, and ClonTech.

DETAILED DESCRIPTION OF THE INVENTION

The present invention relates to a method for identifying and/or obtaining a drug for the amelioration or treatment of a disease or for determining the toxicity of a compound comprising (a) contacting a test sample comprising an in vitro differentiated cell with a test substance to be screened, wherein said cell is induced to display a predefined diseased phenotype which substantially corresponds to a phenotype of a diseased cell, tissue or organ; and (b) determining a responsive change of the phenotype in said test sample, wherein a responsive change (i) preventing or delaying the onset or the progression of the diseased phenotype is indicative for a useful drug; and (ii) enhancing the onset or progression the diseased phenotype is indicative for the toxicity of the compound.

The present invention is based on the observation that in vitro differentiated cardiomyocytes derived from embryonic stem cells upon hormonal stimuli behave in substantially the same way as correspondingly treated heart cells isolated from neonatal rats; see Example 1. In particular, a diseased phenotype could be induced in the in vitro differentiated cells resembling the phenotype observed for diseased adult heart cells. Thus, in accordance with the present invention, it could surprisingly been shown that in vitro differentiated cells are suitable and appropriate to substitute cardiomyopathic cells obtained from the heart and thus can be used for the screening of substances, for example such which influence the response of the cardiomyocytes on hormone stimulation.

Without intending to be bound by theory it is, thanks to the experiments performed in accordance with the present invention, believed that cells derived from multipotent cells, in particular from embryonic stem cells, differentiated in vitro to a particular cell or tissue type can be induced to display a predefined diseased phenotype which substantially resembles the diseased phenotype of cells and tissue derived from a subject suffering from the disease. Thus, for the first time a reliable source of cells is provided, which can be used to study the therapeutic and toxic effects, respectively, of drugs and other compounds. In particular, it is now possible to determine in an in vitro cell-based assay whether a putative drug is capable of preventing the onset of a disease or at least of attenuating its progression; see e.g. Example 3.

Besides the simple availability of standardized cell preparations a further advantage of the use of in vitro differentiated cells consists in that the cells can be easily genetically engineered by various ways, for example by manipulating the multipotent cells such as embryonic stem cells which served as the starting material for the in vitro differentiation.

Cardiomyocytes derived from animals may also be efficiently genetically modified (Sen et al., J. Biol. Chem. 263 (1988), 19132-19136; Bonci et al., Gene Ther. 10 (2003), 630-636). However, such modification has to be performed for each cell preparation, or a transgenic animal must be produced for each and every desired modification in order to obtain cells for the in vitro analysis.

In contrast, the present invention allows the efficient and fast generation of multiple in vitro differentiated cells which are also amenable to screening systems of industrial scale. In this way, for example, embryonic stem cells may also be modified to express a reporter gene in order to ease a read-out of the assay with the in vitro differentiated cells.

Thus, the present invention provides a method for identifying and/or obtaining a drug for the amelioration or treatment of a disease or for determining the toxicity of a compound comprising (a) contacting a test sample comprising an in vitro differentiated cell with a test substance to be screened, wherein said cell is induced to display a predefined diseased phenotype which substantially corresponds to a phenotype of a diseased cell, tissue or organ; and (b) determining a responsive change of the phenotype in said test sample, wherein a responsive change (i) preventing or delaying the onset or the progression of the diseased phenotype is indicative for a useful drug; and (ii) enhancing the onset or progression the diseased phenotype is indicative for the toxicity of the compound.

In order to assess the effect of a test compound on the in vitro differentiated cells, said cells are preferably maintained in starvation medium before the addition of the test compound; see also Examples 1 to 3. In several, non-limiting examples the isolated in vitro differentiated cells are maintained in serum-free medium between about 6 hours to about 4 days, preferably between about 12 hours to about 2 days, and most preferably about 24 hours before the induction of the diseased phenotype, for example by the addition of a physiologically active agent capable of inducing said phenotype and/or the addition of the test compound; see Examples 1 and 3.

In vitro differentiated cells, which have been induced to display a disease phenotype in accordance with the present invention can be used to screen for factors (such as solvents, small molecule drugs, peptides, oligonucleotides) or environmental conditions (such as culture conditions or manipulation) that exert a phenotypic change of such cells. Screening may be done either because the compound is designed to have a pharmacological effect on the cells, or because a compound designed to have effects elsewhere may have unintended side effects on cells of this tissue type. The screening can be conducted using any of the in vitro differentiated cells of the invention.

Generally it can be referred to the standard textbook In vitro Methods in Pharmaceutical Research, Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change. The diseased phenotype as well as the phenotypic changes effected by the test compound on the in vitro differentiated cell contacted with an agent can be assessed by any means known to one of skill in the art. In one embodiment the morphology is examined, for example (electron) microscopy is used to assess the (ultra)structure of the cells; see Example 1 and FIG. 1. Suitable parameters for evaluation include, but are not limited to the evaluation of gap junctions between contacting cells such as cardiomyocytes. In other embodiments, immunohistochemical or immunofluorescence techniques are used to assess the phenotype; see Example 1 and FIG. 2. In yet another embodiment, phenotypic changes are assessed by analysis expression of specific mRNA molecules expressed in the diseased cells. Suitable assay systems include, but are not limited to RT-PCR, in situ hybridization, Northern analysis, or RNase protection assays; see Examples 1 to 3 as well as FIGS. 3 and 4. In a further embodiment the levels of polypeptides expressed in the differentiated cells are assayed. Specific, non-limiting examples of polypeptide assays of use include Western blot analysis, ELISA assay, or immunofluorescence. Alternatively, calcium transients are measured, as described infra.

The assay can also be used to screen the effect of an agent on the function of a cell, e.g. cardiomyocyte function. Any method known to one of skill in the art can be utilized to assess cardiac function. In one embodiment the beating rate of a cardiomyocyte is assayed to identify agents that increase or decrease beating. One method for assessing the beating rate is to observe beating under a microscope. Agents that can be screened in this manner include inotropic drugs, such as sympathomimetic agents. In one embodiment, cells contacted with the agent are compared with a control. Suitable controls include cells not contacted with the agent, or contacted with vehicle alone. Standard values can also be used as a control.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. It can be referred to A. Vickers (375-410) in In vitro Methods in Pharmaceutical Research, Academic Press, 1997) for further elaboration.

Effect of cell function can be assessed using any standard assay to observe phenotype or for example activity of cardiomyocytes, such as marker expression, receptor binding, contractile activity, or electrophysiology in cell culture. Pharmaceutical candidates can also be tested for their effect on contractile activity such as whether they increase or decrease the extent or frequency of contraction. Where an effect is observed, the concentration of the compound can be titrated to determine the median effective dose.

The assays may be simple "yes/no" assays to determine whether there is a responsive change compared to a control. The test compound or a plurality of test compounds can also be subjected to the test cell, preferably embryoid body in different concentrations or dilution series, preferably at doses that correspond to physiological levels of the corresponding type of test compounds. It is thus also possible to easy generate compound profiles in purpose similar to those described in WO00/34525. For example, two or more assays may be used and/or parameters may be assessed. Those assays/parameters can be performed/assessed in parallel or subsequently; or the results of one assay may be compared with results of a corresponding assay performed elsewhere. Once the molecular profile of the test composition is determined, it can be compared to that of a chemical composition with predetermined biological activities or, preferably, to a library of molecular profiles of chemical compositions with predetermined biological activities. The outcome of such comparison provides information for one to predict the likelihood of whether the test composition has the potential of a drug or is toxic, what type of toxicities, and how toxic it would be as compared to the other known toxic compositions.

In a particular embodiment of the present invention said test compound is subjected to the test sample before or during inducing the onset of the diseased phenotype. Performing the method of the invention can be done according to screening methods known in the art employing cell preparations from animals. For example, the effects of doxorubicin (DOX) on intracellular calcium transients and the cardioprotective effects of a calcium antagonist on DOX-induced impairment of calcium handling were examined in neonatal rat cultured cardiac myocytes; see Maeda et al., Jpn. Circ. J. 63 (1999), 123-129. Here, cultured cardiac myocytes isolated from neonatal Wistar-Kyoto rats were treated with DOX for 24 h. Field-stimulated calcium transients in single myocytes were measured in the presence or absence of isoproterenol using fura-2/AM. Calcium transients were also measured after the addition of DOX to myocytes pretreated with the calcium antagonist benidipine. In accordance with the present invention in vitro differentiated cardiomyocytes are used for the screening of cardioprotective compounds. Ichiba et al., J. Mol. Cell. Cardiol. 30 (1998), 1105-1114, describe experiments on the regulation of intracellular calcium concentrations by calcium and magnesium in cardioplegic solutions protects rat neonatal myocytes from simulated ischemia. Likewise, in vitro differentiated cells are subjected to simulated ischemia in accordance with the present invention and used for identifying compounds and factors influencing the cardioprotective effect of cardioplegic solutions.

Differential regulation of phospholipase C-beta isozymes in cardiomyocyte hypertrophy has been described by Schnabel et al., Biochem. Biophys. Res. Commun. 275 (2000), 1-6.

Here, the expression pattern of the PLCbeta isozyme subfamily was investigated in neonatal rat cardiomyocytes after stimulation with different hypertrophic stimuli, and wherein the effect of various compounds such as IGF-I receptor antagonist have been tested by preincubation of the cardiomyocytes with the compound. In accordance with the present invention such compound testing can now be easily and reliably performed with in vitro differentiated cardiomyocytes.

Usually said in vitro differentiated cell is derived from pluri- or multipotent cells, preferably from embryonic stem (ES) cells, most preferably said pluri- or multipotent cell is derived from mouse or rat, or in particular from human.

The invention can be practiced using stem cells of any vertebrate species. Included are stem cells from humans; as well as non-human primates, domestic animals, livestock, and other non-human mammal. Amongst the stem cells suitable for use in this invention are primate pluripotent stem cells derived from tissue formed after gestation, such as a blastocyst, or fetal or embryonic tissue taken any time during gestation. Non-limiting examples are primary cultures or established lines of embryonic stem cells. The invention is also applicable to adult stem cells. It is referred to the literature of Anderson et al., Nat. Med. 7 (2001), 393-395; Gage, Science 287 (2000), 433-438, and Prockop, Science 276 (1997), 71-74, wherein the extraction and culture of those cells is described.

Media for isolating and propagating stem cells can have any of several different formulas, as long as the cells obtained have the desired characteristics, and can be propagated further. Suitable sources include Iscove's modified Dulbecco's medium (IMDM), Gibco, #12440-053; Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; [beta]-mercaptoethanol, Sigma #M7522; human recombinant basic fibroblast growth factor (bFGF), Gibco #13256-029. Exemplary serum-containing ES medium and conditions for culturing stem cells are known, and can be optimized appropriately according to the cell type. Media and culture techniques for particular cell types referred to in the previous section are provided in the references cited herein.

As mentioned before, several sources for ES cells are at the disposal of the skilled person of which human stem cells are preferred for most of the embodiments of the present invention. Human embryonic stem cells and their use for preparing different cell and tissue types are also described in Reprod. Biomed. Online 4 (2002), 58-63. Embryonic stem cells can be isolated from blastocysts of members of the primate species (Thomson et al., Proc. Natl. Acad. Sci. USA 92 (1995), 7844). Human Embryonic Germ (EG) cells can be prepared from primordial germ cells present in human fetal material taken about 8-11 weeks after the last menstrual period. Suitable preparation methods are described in Shamblott et al., Proc. Natl. Acad. Sci. USA 95 (1998), 13726. Method for making cells that resemble embryonic stem cells or embryonic germ cells in morphology and pluripotency derived from primordial germ cells isolated from human embryonic tissue, such as from the gonadal ridges of human embryo, are described in U.S. Pat. No. 6,245,566.

Recently, is has been reported that exfoliated human deciduous tooth, a comparable very accessible tissue, contains multipotent stem cells that were identified to be a population of highly proliferative, clonogenic cells capable of differentiating into a variety of cell types including neural cells, adipocytes, and odontoblasts; see Miura et al., Proc. Natl. Acad. Sci. USA 100 (2003), 5807-5812. After in vivo transplantation, those cells were found to be able to induce bone formation, generate dentin, and survive in mouse brain along with expression of neural markers. Furthermore, multilineage potential of homozygous stem cells derived from metaphase II oocytes has been described in by Lin et al. in Stem Cells 21 (2003), 152-161. Various sources of precursor cells in postnatal muscles and the factors that may enhance stem cell participation in the formation of new skeletal and cardiac muscle in vivo are reviewed in Grounds et al. J. Histochem. Cytochem. 50 (2002), 589-610. Purification of rare Hematopoietic Stem Cell(s) (HSC) to homogeneity that home to bone marrow is described in US2003/0032185. These adult bone marrow cells are described to have tremendous differentiative capacity as they can also differentiate into epithelial cells of the liver, lung, GI tract, and skin. This finding may contribute to clinical treatment of genetic disease or tissue repair. Furthermore, techniques such as nuclear transfer for embryo reconstruction may be employed wherein diploid donor nuclei are transplanted into enucleated MII oocytes. This technology along with other procedures that aid in the establishment of customized embryonic stem (ES) cell lines that are genetically identical to those of the recipient have been reviewed by Colman and Kind, Trends Biotechnol. 18 (2000), 192-196. In order to avoid graft rejection associated with allogenic or xenogenic cells in transplantation syngenic or autologous cells and recipients are preferably used in the corresponding embodiments of the invention. In view of the recent discovered sources of stem cells such as from the bone marrow and tooth it should be possible to accomplish this demand without the need to resort to embryonic cells and tissue. Alternatively, cells may be genetically manipulated to suppress relevant transplantation antigens, see also infra, immunosuppressive agents may be used. The field of stem cell technology is being reviewed by Kiessling and Anderson, Harvard Medical School, in Human Embryonic Stem Cells: An Introduction to the Science and Therapeutic Potential; (2003) Jones and Bartlett Publishers; ISBN: 076372341X.

In order to avoid the use of for example human embryos as the donor for stem cells, which however seems to be justifiable at least under certain circumstances, it may even be possible to employ transgenic non-human animals, in particular mammals as source for embryonic stem cells. For example, compositions and methods for making transgenic swines to be used as xenograft donors is described in U.S. Pat. No. 5,523,226. Likewise, WO97/12035 describes methods of producing transgenic animals for xenotransplantation. Furthermore, immunologically compatible animal tissue, suitable for xenotransplantation into human patients, is described in WO01/88096. Method for making embryonic germ cells from porcine are described for example in U.S. Pat. No. 6,545,199. Cells immunologically compatible with humans can also be employed for purposes of the present invention.

Stem cells can be propagated continuously in culture, using a combination of culture conditions that promote proliferation without promoting differentiation. Traditionally, stem cells are cultured on a layer of feeder cells, typically fibroblast type cells, often derived from embryonic or fetal tissue. The cell lines are plated to near confluence, usually irradiated to prevent proliferation, and then used to support when cultured in medium conditioned by certain cells (e.g. Koopman and Cotton, Exp. Cell 154 (1984), 233-242; Smith and Hooper, Devel. Biol. 121 (1987), 1-91), or by the exogenous addition of leukemia inhibitory factor (LIF). Such cells can be grown relatively indefinitely using the appropriate culture conditions without differentiation.

In the absence of feeder cells, exogenous leukemia inhibitory factor (LIF), or conditioned medium, ES or EG cells spontaneously differentiate into a wide variety of cell types, including cells found in each of the endoderm, mesoderm, and ectoderm germ layers. With the appropriate combinations of growth and differentiation factors, however, cell differentiation can be controlled. For example, mouse ES and EG cells can generate cells of the hematopoietic lineage in vitro (Keller et al., Mol. Cell. Biol. 13 (1993), 473-486; Palacios et al., Proc. Natl. Acad. Sci. USA 92 (1995), 7530-7534; Rich, Blood 86 (1995), 463-472). Additionally, mouse ES cells have been used to generate in vitro cultures of neurons (Bain et al., Developmental Biology 168 (1995), 342-357; Fraichard et al., J. Cell Science 108 (1995), 3161-3188), cardiomyocytes (heart muscle cells) (Klug et al., Am. J. Physiol. 269 (1995), H1913-H1921), skeletal muscle cells (Rohwedel et al., Dev. Biol. 164 (1994), 87-101), vascular cells (Wang et al., Development 114 (1992), 303-316), U.S. Pat. No. 5,773, 255 relates to glucose-responsive insulin secreting pancreatic beta cell lines, U.S. Pat. No. 5,789,246 relates to hepatocyte precursor cells. Hepatic differentiation of murine embryonic stem cells is also described in Jones et al., Exp. Cell Res. 272 (2002), 15-22.

Other progenitors of interest include but are not limited to chondrocytes, osteoblasts, retinal pigment epithelial cells, fibroblasts, skin cells such as keratinocytes, dendritic cells, hair follicle cells, renal duct epithelial cells, smooth and skeletal muscle cells, testicular progenitors, and vascular endothelial cells. Embryonic stem cell differentiation models for cardiogenesis, myogenesis, neurogenesis, epithelial and vascular smooth muscle cell differentiation in vitro have been generally described in Guan et al., Cytotechnology 30 (1999), 211-226.

In vitro differentiated cardiomyocytes, neural cells, hepatocytes, adipocytes, skeletal muscle cells, vascular endothelial cells and osteoblasts are described in US patent application US2002/142457. The preparation of cells of the cardiomyocyte lineage produced from human pluripotent stem cells is described in international application WO03/006950; see also references cited therein. A method for the generation of in vitro differentiated cardiomyocytes from particular stem cells called spoc cells is described in international application WO03/035838. The production of cardiomyocyte-enriched cellular populations, and methods and materials for obtaining the same are also described in international application WO01/68814.

In certain embodiments of the invention, differentiation is promoted by withdrawing one or more medium component(s) that promote(s) growth of undifferentiated cells, or act(s) as an inhibitor of differentiation. Examples of such components include certain growth factors, mitogens, leukocyte inhibitory factor (LIF), and basic fibroblast growth factor (bFGF). Differentiation may also be promoted by adding a medium component that promotes differentiation towards the desired cell lineage, or inhibits the growth of cells with undesired characteristics.

It may be desirable that the cells have the ability to replicate in certain drug screening and therapeutic applications, and to provide a reservoir for the generation of in vitro differentiated cells such as cardiomyocytes and their precursors. The cells of this invention can optionally be telomerized to increase their replication potential, either before or after they progress to restricted developmental lineage cells or terminally differentiated cells. ES cells that are telomerized may be taken down the differentiation pathway described earlier; or differentiated cells can be telomerized directly.

Cells are telomerized by genetically altering them by transfection or transduction with a suitable vector, homologous recombination, or other appropriate technique, so that they express the telomerase catalytic component (TERT), typically under a heterologous promoter that increases telomerase expression beyond what occurs under the endogenous promoter. Particularly suitable is the catalytic component of human telomerase (hTERT), provided in international application WO98/14592. For certain applications, species homologs like mouse TERT (WO99/27113) can also be used. Transfection and expression of telomerase in human cells is described in Bodnar et al., Science 279 (1998), 349, and Jiang et al., Nat. Genet. 21 (1999), 111. In another example, hTERT clones (WO98/14592) are used as a source of hTERT encoding sequence, and spliced into an EcoR1 site of a PBBS212 vector under control of the MPSV promoter, or into the EcoR1 site of commercially available pBABE retrovirus vector, under control of the LTR promoter.

They can then be assessed for hTERT expression by RT-PCR, telomerase activity (TRAP assay), immunocytochemical staining for hTERT, or replicative capacity; see also supra.

Continuously replicating colonies will be enriched by further culturing under conditions that support proliferation, and cells with desirable phenotypes can optionally be cloned by limiting dilution. Depending on the intended use of the cells, other methods of immortalization may also be acceptable, such as transforming the cells with DNA encoding myc, the SV40 large T antigen, or MOT-2 (U.S. Pat. No. 5,869,243; international applications WO97/32972 and WO01/23555).

In accordance with this invention, populations of differentiated cells to be used in the assay are preferably depleted of relatively undifferentiated cells and/or of cells of undesired cell types by using a selection system that is lethal to the undesired cells and cell types, i.e. by expressing a selectable marker gene that renders cells of a specific cell type resistant to a lethal effect of an external agent, under control of a regulatory sequence that causes the gene to be preferentially expressed in the desired cell type and/or at a certain stage of development. To accomplish this, the cells are genetically altered before the process used to differentiate the cells into the desired lineage for therapy, in a way that the cells comprises a selectable marker operably linked to a first cell type specific regulatory sequence specific for the desired first cell type.

Any suitable expression vector for this purpose can be used. Suitable viral vector systems for producing stem cells altered according to this invention can be prepared using commercially available virus components. The introduction of the vector construct or constructs into the embryonic stem cells occurs in a known manner, e.g. by transfection, electroporation, lipofection or with the help of viral vectors. Viral vectors comprising effector genes are generally described in the publications referenced in the last section. Alternatively, vector plasmids can be introduced into cells by electroporation, or using lipid/DNA complexes. Exemplary is the formulation Lipofectamine 2000™, available from Gibco/Life Technologies. Another exemplary reagent is FuGENE™ 6 Transfection Reagent, a blend of lipids in non-liposomal form and other compounds in 80% ethanol, obtainable from Roche Diagnostics Corporation. Preferably, the vector constructs and transfection methods described in WO02/051987 are used; the disclosure content of which is incorporated herein by reference.

Resistance genes per se are known. Examples for these are nucleoside and aminoglycoside-antibiotic-resistance genes, e.g. puromycin (puromycin-N-acetyltransferase), streptomycin, neomycin, gentamycin or hygromycin. Further examples for resistance genes are dehydrofolate-reductase, which confers a resistance against aminopterine and methotrexate, as well as multi drug resistance genes, which confer a resistance against a number of antibiotics, e.g. against vinblastin, doxorubicin and actinomycin D.

In a particularly preferred embodiment of the present invention, said selectable marker confers resistance to puromycin. Puromycin is particularly suited for the fast elimination of non-cardiac cells in adherent culture of transgenic EBs; see also Examples. Furthermore, drug selection of cardiac cells can be implemented entirely in the suspension culture of transgenic EBs. Hence, it could also be shown that purified ES derived cardiomyocytes survive much longer in culture than untreated counterparts. Moreover, the elimination of undifferentiated ES cells during drug selection process has itself been shown to have clear positive effect on viability and longevity of such differentiated ES derived cells as cardiomyocytes. In addition, it could be surprisingly shown that the release from surrounding non-differentiated cells induces proliferation of cardiomyocytes. Thus, the drug selection possesses both purifying and multiplying effect.

In a preferred embodiment of the invention, said ES cell of said ES cell-derived first cell type comprises a reporter gene, wherein said reporter is operably linked to a cell type specific regulatory sequence specific for said first cell type. This type of vector has the advantages of providing visualization of differentiation, definition of the time point for beginning of drug selection, visualization of drug selection and tracing of the fate of purified cells grafted in recipient tissue. Such vectors, which are preferably employed in accordance with the methods of the present invention are described in WO02/051987. Usually, said cell type specific regulatory sequence of the reporter gene is substantially the same as said first cell type specific regulatory sequence of the marker gene. This can advantageously be achieved by putting said marker gene and said reporter gene into the same recombinant nucleic acid molecule, i.e. vector used for stem cell transfection, preferably such that said marker gene and said reporter gene are contained on the same cistron.

The reporter can be of any kind as long as it is non-damaging for the cell and confers an observable or measurable phenotype. According to the present invention, the green fluorescent protein (GFP) from the jellyfish *Aequorea victoria* (described in WO95/07463, WO96/27675 and WO95/21191) and its derivates "Blue GFP" (Heim et al., Curr. Biol. 6 (1996), 178-182 and "Redshift GFP" (Muldoon et al., Biotechniques 22 (1997), 162-167) can be used. Particularly preferred is the Enhanced Green Fluorescent Protein (EGFP). Further embodiments are the Enhanced Yelow and Cyan Fluorescent Proteins (EYFP and ECFP, respectively) and Red Fluorescent proteins (DsRed, HcRed). Further fluorescent proteins are known to the person skilled in the art and can be used according to the invention as long as they do not damage the cells. The detection of fluorescent proteins takes places through per se known fluorescence detection methods; see, e.g., Kolossov et al., J. Cell Biol. 143 (1998), 2045-2056. Alternatively to the fluorescent proteins, particularly in in vivo applications, other detectable proteins, particularly epitopes of those proteins, can also be used. Also the epitope of proteins, though able to damage the cell per se, but whose epitopes do not damage the cells, can be used; see also WO02/051987.

For the selection for stably transfected ES cells vector constructs contain a further selectable marker gene, which confers e.g. a resistance against an antibiotic, e.g. neomycin. Of course, other known resistance genes can be used as well, e.g. the resistance genes described above in association with the fluorescent protein encoding genes. The selection gene for the selection for stably transfected ES cells is under the control of a different promoter than that which regulates the control of the expression of the detectable protein. Often constitutively active promoters are used, e.g. the PGK-promoter.

The use of a second selection gene is advantageous for the ability to identify the successfully transfected clones (efficiency is relatively low) at all. Otherwise a smothering majority of non-transfected ES cell may exist and during differentiation e.g. no EGFP positive cells might be detected.

In a further embodiment of the invention the cells can be manipulated additionally so that specific tissues are not formed. This can occur for instance by inserting of repressor elements, e.g. a doxycyclin inducible repressor element. Thereby, a possible contamination of the desired differentiated cells with pluripotent, potentially tumorigenic cells can be excluded.

The desired cell type intended for the stem cell to differentiate to may be of any kind and includes but not limited to neuronal cells, glial cells, cardiomyocytes, glucose-responsive insulin secreting pancreatic beta cells, hepatocytes, astrocytes, oligodendrocytes, chondrocytes, osteoblasts, retinal pigment epithelial cells, fibroblasts, keratinocytes, dendritic cells, hair follicle cells, renal duct epithelial cells, vascular endothelial cells, testicular progenitors, smooth and skeletal muscle cells; see also supra.

In a particular preferred embodiment of the invention, said in vitro differentiated cells are cardiomyocytes. For this embodiment, said cell type specific regulatory sequence is preferably atrial and/or ventricular specific. Corresponding regulatory sequences, i.e. cardiac specific promoters are described in the prior art; see also supra. For example Nkx-2.5 specific for very early cardiomyocytes and mesodermal precursor cells, respectively, (Lints et al., Development 119 (1993), 419-431); human-cardiac-α-actin specific for heart tissue, (Sartorelli et al., Genes Dev. 4 (1990), 1811-1822), and MLC-2V specific for ventricular heart muscle cells (O'Brien et al., Proc. Natl. Acad. Sci. USA. 90 (1993), 5157 5161; Lee et al., Mol. Cell. Biol. 14 (1994), 1220-1229; Franz et al., Circ Res. 73 (1993), 629-638 and WO96/16163). The cardiac specific alpha-myosin heavy chain promoter is described in Palermo et al., Cell. Mol. Biol. Res. 41 (1995), 501-519 and Gulick et al., J. Biol. Chem. 266 (1991), 9180-91855. The expression of the atrial specific myosin heavy chain AMHC1 and the establishment of anteroposterior polarity in the developing chicken heart is described in Yutzey et al., Development 120 (1994), 871-883.

Another cell type are fibroblasts can also be generated de novo from ES cells in accordance with the method of the present invention. Thus, ES cells are transfected with a recombinant nucleic acid molecule comprising a marker and optionally reporter gene operatively linked to a cell type specific regulatory sequence, i.e. fibroblast specific promoter such as the a2 (I) collagen promoter though also active in bone cells; Lindahl et al., Biol. Chem. 277 (2002), 6153-6161; Zheng et al., Am. J. Pathol. 160 (2002), 1609-1617; Antoniv et al., J. Biol. Chem. 276 (2001), 21754-21764; see also Finer, et al., J. Biol. Chem. 262 (1987), 13323-13333; Bou-Gharios et al., J. Cell. Biol. 134 (1996), 1333-1344; Zheng et al., Am. J. Pathol. 160 (2002), 1609-1617; Metsaranta et al., J. Biol. Chem. 266 (1991), 16862-16869.

A further cell type are endothelial cells which can be derived from ES cells transfected with a vector construct as generally described before, wherein said cell type specific regulatory sequence is an endothelial specific promoter; see, e.g., vascular endothelial-cadherin promoter described by Gory et al., Blood 93 (1999), 184-192; the Tie-2 promoter/enhancer by Schlaeger et al., Proc. Natl. Acad. Sci. USA 94 (1997), 3058-3063; the Flk-1 promoter/enhancer by Kappel et al., Biochem. Biophys. Res. Commun. 276 (2000), 1089-1099.

Further cell and tissue type specific promoters are known; see, e.g., chondrocyte specific pro-alpha1 (II) collagen chain (collagen 2) promoter fragment described by Zhou et al., J. Cell Sci. 108 (1995), 3677-3684; neural alpha-1-tubulin specific promoter described in Gloster et al., J Neurosci 14 (1994); 7319-7330 and glial fibrillary acidic protein (GFAP) promoter in Besnard et al., J. Biol. Chem. 266 (1991), 18877-18883. Further examples for tissue specific promoters are those, which are active in glia cells, hematopoietic cells, neuronal cells, preferably embryonal neuronal cells endothelial cells, cartilage cells or epidermal cells as well as insulin secreting β-cells. "Tissue specific" is to be subsumed under the term "cell specific".

Further examples for non-heart-specific promoters are: PECAMI, FLK-1 (endothelium), nestine (neuronal precursor cells), tyrosin-hydroxylase-1-promoter (dopaminergic neurons), smooth muscle α-actin, smooth muscle myosin (smooth muscles), α1-fetoprotein (endoderm), smooth muscle heavy chain (SMHC minimal promoter (specific for smooth muscles, (Kallmeier et al., J. Biol. Chem. 270 (1995), 30949-30957).

The term development specific promoter refers to promoters, that are active during certain points of time during development. Examples for such promoters are the β-MHC promoter that is expressed during embryonal development in the ventriculum of the mouse and is superseded by the α-MHC promoter in the prenatal phase. NKx2.5, a promoter during the early mesoderm/heart development, atrial-natriuretic-factor, a marker of the early embryonal heart with exception of the pacemaker, that is down regulated also in later developmental stages, Flk-1, an endothelium specific promoter that is active during the early vasculogenesis, intron 2-segment of the nestine gene that is expressed in neuronal precursor cells (embryonal neurons and glia cells) and adult glia cells (partially still able to divide) (Lothian and Lendahl, Eur. J. Neurosci. 9 (1997), 452-462U).

For the embodiments described hereinbefore, said resistance gene and said reporter gene are preferably contained in a bicistronic vector and are preferably separated by an IRES. Particular preferred is the use of a construct, wherein said resistance gene confers resistance to puromycin, said marker is EGFP and said promoter is the cardiac αMHC promoter; see also the Examples.

It is known that every tissue consists of a main specific cell type which determines its functional role along with supporting cell types (e.g. fibroblasts, stromal, endothelial, glial cells, etc.), which can be important for maintaining of three-dimensional architectonic structure of tissue, its trophic function and interconnections with other tissue systems of the whole organism. Therefore, in one embodiment of the method of the present invention an in vitro differentiated cell of one cell type is cocultured with at least one cell of a second cell type, and/or comprised in tissue or tissue-like structures comprising at least one second cell type such as any one of those described hereinbefore. Said second cell type may be for example an embryonic second cell type. Preferably, the in vitro differentiated cell in said tissue or tissue-like structure is obtained by culturing an embryonic stem (ES) cell derived first cell type in the presence of at least one embryonic second cell type; and allowing integration and alignment of said at least two cell types into tissue or tissue-like structures. Said at least second cell type may also be generated as the first cell type, i.e. by in vitro differentiation of ES cells which have been genetically engineered with corresponding marker genes; see also supra for appropriate methods and materials. A corresponding method for providing a variety of tissue or tissue-like structures and like in vitro differentiated cells and tissue is described in detail in international application WO2004/113515 the disclosure content of which is incorporated herein by reference.

Accordingly, the term "in vitro differentiated cell" is also meant to include a plurality of in vitro differentiated cells of the same or different cell types as well as in vitro differentiated tissue and organs, and cocultures of in vitro differentiated cells with other cell types such as of embryonic origin. Thus, the term "in vitro differentiated cell" does not necessarily exclude the presence of a cell or cell type other than that which the original stem cell has been differentiated to. However, in most embodiments the use of a substantially pure culture of in vitro differentiated cells is preferred or the use of even a single cell.

In one embodiment, wherein said in vitro differentiated cell is a cardiomyocyte said at least second cell type preferably corresponds to an endothelial cell and/or fibroblast. For example, it has been reported that bradykinin blocks angiotensin II-induced hypertrophy in the presence of endothelial cells; see Ritchie et al., Hypertension 31 (1998), 39-44. In those experiments effects of bradykinin on isolated ventricular cardiomyocytes from adult and neonatal rat hearts have been determined and the extent to which bradykinin blocks hypertrophy in vitro. Bradykinin was found to be a hypertrophic agonist, as defined by increased protein synthesis and atrial natriuretic peptide secretion and expression. However, in cardiomyocytes cocultured with endothelial cells, bradykinin did not increase protein synthesis. In conclusion, bradykinin has a direct hypertrophic effect on ventricular myocytes. The presence of endothelial cells is required for the antihypertrophic effects of bradykinin.

Thus, depending on the nature of the disease and the type of diseased tissue or organ to be investigated the use of cocultures of differentiated cells or in vitro differentiated tissue in the method of the present invention may be taken into account.

As mentioned above, the in vitro differentiated cell to be tested is obtained by a method which is preferably performed such that it allows self-assembly of the different cell types, for example into the desired tissue or tissue-like structures that should reflect the tissue or organ of a mammal, preferably human, that is supposed to be exposed to a given compound. The stem cells are in a preferred embodiment of the invention available in form of aggregates that are known as embryoid bodies (EBs). WO02/051987 describes a protocol to obtain embryoid bodies. The manufacturing takes place preferably with the "hanging drop" method or by methylcellulose culture (Wobus et al., Differentiation 48 (1991), 172-182).

Hence, in a particular preferred embodiment, the functional tissue assay of the present invention is performed with embryoid bodies (EBs).

As mentioned before, embryoid bodies represent a complex group of cells differentiating into different tissues. In one embodiment, the cells within an embryoid body are substantially synchronized for their differentiation. Accordingly, at known intervals, the majority of the synchronized cells differentiate into the three embryonic germ layers and further differentiate into multiple tissue types, such as cartilage, bone, smooth and striated muscle, and neural tissue, including embryonic ganglia; see also Snodgrass et al., "Embryonic Stem Cells: Research and Clinical Potentials" in Smith and Sacher, eds. Peripheral Blood Stem Cells American Association of Blood Banks, Bethesda Md. (1993). Thus, the cells within embryoid bodies provide a much closer model to the complexity of whole organisms than do traditional single cell or yeast assays, while still avoiding the cost and difficulties associated with the use of mice and larger mammals. Moreover, the recent availability of human embryoid bodies improves the predictive abilities of the invention by providing an even closer vehicle for modeling toxicity and identification of drugs useful for the treatment of heart disorders in human organ systems, and in humans.

Alternatively to this, spinner flasks (stirring cultures) can be used as culture method. Therefor, the undifferentiated ES cells are introduced into stirring cultures and are mixed permanently according to an established procedure. Therefore, 10 million ES cells are introduced into 150 ml medium with 20% FCS and are stirred constantly with the rate of 20 rpm., wherein the direction of the stirring motion is changed regularly. 24 hours after introduction of the ES cells an extra 100 ml medium with serum is added and thereupon 100-150 ml of the medium is exchanged every day (Wartenberg et al., FASEB J. 15 (2001), 995-1005). Under these culture conditions large amounts of ES cell-derived cells, i.e. cardiomyocytes, endothelial cells, neurons etc. depending on the composition of the medium can be obtained. The cells are selected by means of the resistance gene either still within the stirring culture or after plating, respectively.

Alternatively to this, the EBs differentiated in the hanging drop might be not plated, but kept simply in suspension. Even under these conditions a progression of a differentiation could be observed experimentally. The washing off of the non-desired cell types can be done with mechanical mixing alone and addition of low concentration of enzyme (e.g. collagenase, trypsin); a single cell suspension is achieved with easy washing off of the non-desired cell types.

In a particular preferred embodiment of the present invention, embryoid bodies are prepared according a recent developed "mass culture" system employed in the appended examples and described in detail in international application WO2005/005621.

In a preferred embodiment of the method of the present invention, the disease said diseased phenotype corresponds to is a heart disease such as heart failure or a cardiomyopathy. Most preferably, the diseased phenotype to be induced and assessed is a cardiac hypertrophic phenotype; see also the Examples.

Heart failure is the inability of the heart to supply sufficient oxygenated blood to meet the metabolic needs of the tissues and cells in a subject. This can be accompanied by circulatory congestion, such as congestion in the pulmonary or systemic veins. As used herein, the term heart failure encompasses heart failure from any cause, and is intended herein to encompass terms such as "congestive heart failure," "forward heart failure," "backward heart failure," "high output heart failure," "low output heart failure," and the like; see also Chapters 13-17 in Braunwald for a detailed discussion. Conditions that could lead to heart failure include, but are not limited to, coronary artery disease, cardiomyopathy, or congenital heart disease. Cardiomyopathy is any disease or dysfunction of the myocardium (heart muscle) in which the heart is abnormally enlarged, thickened and/or stiffened. As a result, the heart muscle's ability to pump blood is usually weakened. The disease or disorder can be, for example, inflammatory, metabolic, toxic, infiltrative, fibroplastic, hematological, genetic, or unknown in origin. There are two general types of cardiomyopathies: ischemic (resulting from a lack of oxygen) and non-ischemic. Ischemic cardiomyopathy is a chronic disorder caused by coronary artery disease—a disease in which there is atherosclerotic narrowing or occlusion of the coronary arteries on the surface of the heart. Coronary artery disease often leads to episodes of cardiac ischemia, in which the heart muscle is not supplied with enough oxygen-rich blood. Eventually, the heart muscle enlarges from the additional work it must do in the absence of sufficient oxygen-rich blood.

Non-ischemic cardiomyopathy is generally classified into three groups based primarily on clinical and pathological characteristics:

(1) dilated cardiomyopathy, a syndrome characterized by cardiac enlargement and impaired systolic function of one or both ventricles;

(2) hypertrophic cardiomyopathy, herein defined as (a) global or regional increase in thickness of either ventricular wall or the interventricular septum, or (b) an increased susceptibility to global or regional increase in thickness of either ventricular wall or the interventricular septum, such as can occur in genetic diseases, hypertension, or heart valve dysfunction; or (3) restrictive and infiltrative cardiomyopathies, a group of diseases in which the predominant clinical feature is usually impaired ability of the heart to relax (diastolic dysfunction), and is often characterized by infiltration of the heart muscle with foreign substances such as amyloid fibers, iron, or glycolipids; see also Wynne and Braunwald, The cardiomyopathies and myocarditides, Braunwald et al., eds., Harrison's principles of internal medicine, $15^{th}$ ed. New York, McGraw-Hill (2001), 1359-1365.

With respect to the use of cardiomyocytes as the in vitro differentiated cells in accordance with the method of the present invention, said phenotype preferably includes a parameter selected from the group consisting of cell size, cell shape, protein synthesis, organization of actin/myosin filament, activation of gene expression pattern characteristic of cardiomyopathic cells, and/or activation of genes expressed during early embryonic development; see also infra.

Of course, other cell types such as hepatocytes can also be assessed in accordance with the present invention, for which appropriate parameters for determining phenotypic changes are well known in the art. For example, WO01/81549 describes the generation of in vitro differentiated cells derived from pluripotent stem cells with morphological features of hepatocytes, expressing surface markers characteristic of hepatocytes, and having enzymatic and biosynthetic activity important for liver function. The cells can be characterized according to a number of phenotypic criteria. The criteria include but are not limited to the detection or quantitation of expressed cell markers, and enzymatic activity, and the characterization of morphological features and intercellular signaling. The features are readily appreciated by those skilled in evaluating such things, and include any or all of the following: a polygonal cell shape, a binucleate phenotype, the presence of rough endoplasmic reticulum for synthesis of secreted protein, the presence of Golgi-endoplasmic reticulum lysosome complex for intracellular protein sorting, the presence of peroxisomes and glycogen granules, relatively abundant mitochondria, and the ability to form tight intercellular junctions resulting in creation of bile canalicular spaces. Cell markers useful in distinguishing liver progenitors, hepatocytes, and biliary epithelium, are shown in Table 1 of WO01/81549. Other markers of interest include those exemplified in Examples 1, 2, and 6, of that international application.

For example, the expression of cytochrome p450 can also be measured at the protein level, for example, using specific antibody in Western blots, or at the mRNA level, using specific probes and primers in Northern blots or RT-PCR; see Borlakoglu et al., Int. J. Biochem. 25 (1993), 1659. Particular activities of the p450 system can also be measured: 7-ethoxycoumarin O-de-ethylase activity, aloxyresorufin O-de-alkylase activity, coumarin 7-hydroxylase activity, p-nitrophenol hydroxylase activity, testosterone hydroxylation, UDP-glucuronyltransferase activity, glutathione S-transferase activity, and others; see, e.g., review by Gomes-Lechon et al. in "In vitro Methods in Pharmaceutical Research" Academic Press (1997), 411-431.

As already described above, the diseased phenotype is preferably induced during culturing the in vitro differentiated cell, since the diseases phenotype may be lethal for the stem cell used for differentiation. Furthermore, the possibility to induce the diseased phenotype allows investigation whether a given compound is capable of preventing the onset of a disease if added prior to the induction of the diseased phenotype. This embodiment is particularly useful for identifying and obtaining drugs that can be used as a prophylactic means, which is especially worthwhile to consider for the prevention of heart diseases. However, as demonstrated in Example 2, it is also possible and envisaged in accordance with the present invention to confer the diseased phenotype in a constitutive manner, for example by constitutive expression of a disease-related gene.

In one preferred embodiment, said phenotype in the method of the present invention is induced by culturing the in vitro differentiated cell in the presence of a physiologically active compound. As demonstrated in Examples 1 and 3, this can be done for cardiomyocytes with a hypertrophic agonist such as preferably endothelin-1, angiotensin II, or an $\alpha$1-adrenergic agonist, most preferably said $\alpha$1-adrenergic agonist is phenylephrine.

As mentioned before and described in Example 2, in another embodiment the in vitro differentiated cell is genetically engineered to display said phenotype. Genetically engineering can be done by various means. For example, the in vitro differentiated cell can be transduced using standard procedures known in molecular biology in order to introduce a nucleic acid molecule of interest into the cell. In one embodiment, the nucleic acid molecule encodes a polypeptide the expression of which confers the diseased phenotype. The polypeptide encoded by the nucleic acid molecule can be from the same species as the cells (homologous) or can be from a different species (heterologous). Furthermore, the polypeptide may either correspond to a wild-type or a mutant allele either of which may be responsible for the diseased phenotype. The polypeptide may be of any kind, for example an enzyme, structural protein or transcriptional regulator.

Usually, the nucleic acid sequence of interest is operably linked to a regulatory element, such as a transcriptional and/or translational regulatory element; see also supra. Regulatory elements include elements such as a promoter, an initiation codon, a stop codon, mRNA stability regulatory elements, and a polyadenylation signal. A promoter can be a constitutive promoter or an inducible promoter. Specific non-limiting examples of promoters include the CMV promoter, an atrial natriuretic factor promoter, and promoters including TET-responsive element for inducible expression of transgene. In another embodiment, the nucleic acid sequence of interest is inserted into a vector, such as an expression vector. Procedures for preparing expression vectors are known to those of skill in the art and can be found in Sambrook et al., Molecular Cloning: A Laboratory Manual, 2nd Ed., Cold Spring Harbor Press, Cold Spring Harbor, N.Y. (1989).

Said phenotype can be due to (over)expression of a (mutated) gene, knock-down of gene(s) (e.g. by RNA interference; RNAi), knock-out, or knock-in of (a) gene(s) in said in vitro differentiated cell.

In one embodiment, an in vitro differentiated cell or the underlying ES cells may be transfected with a nucleic acid molecule designed to functionally delete or "knock-out" a gene of interest. In this method, the nucleic acid molecule of interest is a nucleic acid molecule that undergoes homologous recombination and is inserted into the genome of the cell. Methods for producing "knock-outs" in ES cells are known to one of skill in the art (see, e.g., U.S. Pat. No. 5,939,598). According to this example, cells are cultured in vitro as described herein and an exogenous nucleic acid is introduced into the cells by any method known to one of skill in the art, for example, by transfection or electroporation. The transfected cultured cells can then be studied in vitro. Methods for the introduction of nucleic acid sequences into stem cells are known in the art (e.g., see U.S. Pat. No. 6,110,743). However, it is also possible to transfect the differentiated cell, using for example adenoviral gene transfer; see, e.g., Larbig et al., Circulation 107 (2003), 485-489.

Calcium is central in the regulation of cardiac contractility, growth and gene expression. Variations in the amplitude, frequency and compartmentalization of calcium signals are decoded by calcium/calmodulin-dependent enzymes, ion channels and transcription factors. The circuitry for calcium signaling creates opportunities for pharmacological modification of cardiac function and thus provides a multitude of putative target genes for use in the method of the present invention; see for review, e.g., Frey et al., Nature Med. 6 (2000), 1221-1227.

Phenotypic diversity in hypertrophic cardiomyopathy and molecular pathways that result in cardiac hypertrophy and the factors that modify these processes are discussed in Arad et al., Hum. Mol. Gen. 11 (2002), 2499-2506, which describes that hypertrophic cardiomyopathy (HCM), once considered 'idiopathic', is now recognized to result from dominant mutations in genes encoding the proteins of the contractile apparatus such as mutations in genes encoding cardiac myosin heavy chain ($\beta$MHC), cardiac myosin binding protein C (MyBPC), cardiac troponin T (TnT), cardiac troponin I (TnI), $\alpha$ tropomyosin ($\alpha$TM), essential and regulatory light chains, and cardiac actin. These genes can serve as parameters to be assessed with respect to the diseased phenotype as well as target genes for inducing a diseased phenotype, in particular a hypertrophic phenotype.

The genetics of dilated cardiomyopathy including the heterogeneity in the clinical features of dilated cardiomyopathy resulting from a single gene mutation are described in Schönberger et., Am. J. Hum. Genet. 69 (2001), 249-260. Table 1 of Schönberger et al. provides an overview for loci with dilated cardiomyopathy as the predominant phenotype. These genes can serve as parameters to be assessed with respect to the diseased phenotype as well as target genes for inducing a diseased phenotype, in particular a dilated cardiomyopathic phenotype.

One particular candidate gene thought to be responsible for cardiomyopathy is phopholamban; see McTiernan et al., J. Mol. Cell. Cardiol. 31 (1999), 679-692, for information on the structure and expression the human phospholamban gene. Phospholamban is an endogenous inhibitor of sarcoplasmic reticulum calcium ATPase and plays a prime role in cardiac contractility and relaxation. Recently, it has been reported that human phospholamban null results in lethal dilated cardiomyopathy revealing a critical difference between mouse and human; see Haghighi et al., J. Clin. Invest. 111 (2003), 869-876. Hence, phopholamban may be further investigated using the in vitro differentiated cell-based assay of the present invention. Means and methods for mediating expression or suppression of the phospholamban gene as well as of mutants thereof are well known to those skilled in the art; see supra and, for example, Eizema et al., Circulation 101 (2000), 2193-2199, reporting on adenovirus-based phospholamban antisense expression as an approach to improve cardiac contractile dysfunction and comparison of a constitutive viral versus an endothelin-1-responsive cardiac promoter. Furthermore, genes may be employed, which hitherto have been considered for the generation of transgenic animal models and treatment for heart diseases. For example, an alpha-myosin heavy chain promoter operatively linked to a coding sequence comprising DNA coding for a beta1-adrenergic receptor is described in U.S. Pat. No. 6,218,597. Over-expression of Gsalpha, and beta-adrenergic receptor antagonists have been used to establish a transgenic animal model of heart failure in international application WO97/36477.

Furthermore, a heart muscle specific expression cassette comprising a nucleotide sequence encoding a human cardiomyopathy inducer under the control of a myocardium-specific regulatory sequence is described in German patent application No. 198 151 28.

The use of a coding region which encodes calcineurin, calcium calmodulin dependent kinase IV (CaMKIV), or a functional fragment of calcineurin or CaMKIV, operatively linked to a promoter that is preferentially active in cardiomyocytes has been described to produce cardiac hypertrophy in transgenic mice; see U.S. Pat. No. 6,657,104 and Example 2. Furthermore, genes which are differentially expressed in hypertrophic cardiac tissue as compared to normal cardiac tissue have been described in US patent application US2003/148296. Described are a panel of genes that are differentially expressed in cardiac hypertrophic states, which have been distinguished in "good" (exercised-induced) cardiac hypertrophy and "bad" (hypertensive-induced) cardiac hypertrophy; see, e.g., table 2 for 20 cardiac hypertrophy marker genes. Further cardiac hypertrophy marker genes are described in international application WO99/24571.

In a preferred embodiment of the method of the present invention, said in vitro differentiated cell (over)expresses a polypeptide selected from the group consisting of (mutant) troponin, heavy myosin chain, calcineurin, calmodulin, protein kinase C, phospholamban or calcium calmodulin dependent kinase IV (CaMKIV).

Another example is provided by Andersen mutations of KCNJ2, which suppress the native inward rectifier current IK1 in a dominant-negative fashion. The Andersen's syndrome is a hereditary disease, which is characterized by cardiac arrhythmias, periodic paralysis and dysmorphic features. Mutations of the KCNJ2 gene, which encodes the inward rectifying potassium channel subunit Kir2.1, have been identified in affected individuals. Expressing the disease mutant KCNJ2-S136F in neonate rat cardiomyocytes using adenoviral gene transfer, it could be shown that I(K1) density was indeed significantly reduced in KCNJ2-S136F-infected cells and that the dominant-negative suppression of I(K1) in native cells is the pathophysiological correlate of the Andersen's syndrome; see Lange et al., Cardiovasc. Res. 59 (2003), 321-327.

Furthermore, it is also possible to use the assay system of the present invention to investigate potential drug target genes. For example, in accordance with the present invention stem cells can be transfected with a plasmid vector comprising a cDNA sequence of a gene which has been identified in context with its differential expression in a diseased cell, tissue or organ. Upon differentiation target gene expression is induced and the resultant phenotype analyzed compared to a control which either does not express the target gene or expresses the target gene at a normal level. If the induction of target gene expression results in a diseased phenotype, e.g. an enhanced diseased phenotype, this may be taken as evidence that the target gene is responsible or at least involved in disease development, and thus may be focused on for therapeutic intervention. Accordingly, in one embodiment of the present invention said in vitro differentiated cell is genetically engineered to express or suppress a gene encoding potential drug target; see also infra.

As already mentioned for the embodiments comprising the use of physiologically active agents for the induction of the diseased phenotype, it is likewise preferred that in in vitro differentiated cells, which have been genetically engineered to display the diseased phenotype, said phenotype is inducible, for example, by expressing the gene responsible for said phenotype under the control of an inducible promoter. Inducible promoter systems are known to the person skilled in the art; see also supra. The promoters employed are preferably inducible and useful under appropriate conditions to direct high-level expression target gene. The use of an inducible promoter in the present invention provides a molecular switch capable of turning on expression of the polynucleotide sequence which is operatively linked when such expression is desired, or turning off the expression when expression is not desired. Examples of inducible promoters include, but are not limited to a metallothioneine promoter, a glucocorticoid promoter, a progesterone promoter and a tetracycline promoter. Numerous expression vector systems exist that can be employed for use with the present invention. For example, Stratagene's Complete Control™ relates to an inducible mammalian expression system, which involves a synthetic ecdyson-inducible promoter. Another example of an inducible expression system is available from Invitrogen, which carries the T-REX™ (tetracycline-regulated expression) system, an inducible mammalian expression system that uses the full-length CMV promoter. The tetracycline-inducible system for regulation of gene expression in transgenic mice is described in Grill et al., Transgenic Res. 12 (2003), 33-43. Furthermore, tetracycline-regulated gene expression in replication-incompetent herpes simplex virus vectors is described by Schmeisser et al., Hum. Gene Ther. 13 (2002), 2113-2124. In addition, the rapid generation of a tetracycline-inducible BCR-ABL defective retrovirus using a single autoregulatory retroviral cassette is provided in Dugray et al., Leukemia 15 (2001), 1658-1662. The use of the tetracycline-controlled transcriptional silencer (tTS) to eliminate transgene leak in inducible overexpression transgenic mice is described in Zhu et al., J. Biol. Chem. 276 (2001), 25222-25229. The Tet-On system in transgenic mice for inhibition of the mouse pdx-1 gene activity by antisense RNA expression in pancreatic beta-cells is reported by Lottmann et al., J. Mol. Med. 79 (2001), 321-328. For doxycycline inducible gene expression see, e.g., Lindeberg et al., J. Neurosci. Res. 68 (2002), 248-253 and Kim et al., Am. J. Pathol. 162 (2003), 1693-1707. Furthermore, the use of doxycycline-controlled gene expression to reversibly alter milk-protein composition in transgenic mice is described in Soulier et al., Eur. J. Biochem. 260 (1999), 533-539. All the inducible expression system can be employed in accordance with the vectors and methods of the present invention.

Furthermore, it is of course to be understood that the gene responsible for said phenotype can be a gene, for example cDNA encoding a RNA, which either may be functional itself such as ribosomal RNA or may encode the functional polypeptide that is responsible for said phenotype. Alternatively, the gene responsible for the induction of said phenotype is capable of mediating the suppression of an endogenous target gene or inhibition of the activity of the product encoded by said target gene. In this case, the lack of expression of the target gene and activity of its gene product would be responsible for the diseased phenotype. It is also to be understood that the target gene to be expressed or suppressed can be a wild-type or mutant allele. Means and methods for conferring expression or suppression of a gene are well known to the person skilled in the art; see also supra.

In order to investigate the prophylactic effect of a test compound it is preferred to induce the diseased phenotype only after the test compound has been added to the culture medium or injected into the cell; see also supra. On the other hand, if it is aimed at determining the therapeutic and curing effect of a putative drug on a disease which has already established, a diseased phenotype may also be induced before the test compound is added and then monitor the progression of the disease in the presence and absence of the test compound, respectively.

In a further embodiment, said method is performed on an array. Arrays for use in the assay of the present invention usually comprise a solid support and attached thereto or suspended thereon the in vitro differentiated cells. The use of planar microelectrode arrays for cultured cells and cell aggregates as biosensors is of particular interest. Such arrays generally consist of a substrate of glass, plastic or silicon over which a conductor, e.g. gold, platinum, indium-tin-oxide, iridium, etc., is deposited and patterned. An insulating layer, e.g. photoresist, polyimide, silicon dioxide, silicon nitride, etc., is deposited over the conducting electrodes and interconnects and then removed in regions over the electrodes to define the recording sites. Cells are cultured directly on this surface and contact the exposed conductor at the deinsulated recording sites. Depending on the size of the electrodes and the cells, recordings of electrical activity can be from a single cell or populations of cells including cell aggregates. Each electrode site is generally connected to the input of a high input impedance, low noise amplifier, with or without AC coupling capacitors, to allow amplification of the relatively small extracellular signals. Examples of such biosensors are described by Novak et al. IEEE Transactions on Biomedical Engineering BME-33(2) (1986), 196-202; Drodge et al., J. Neuroscience Methods 6 (1986), 1583-1592; Eggers et al., Vac. Sci. Technol. B8(6) (1990), 1392-1398; Martinoia et al., J. Neuroscience Methods 48 (1993), 115-121; Maeda et al., J. Neuroscience 15 (1995), 6834-6845; and Mohr et al. Sensors and Actuators B-Chemical 34 (1996), 265-269.

In the embodiment, the method of the present invention is preferably performed with a multi- or microelectrode array (MEA), such as those mentioned above. This assay system of the present invention is a particular advantageous alternative for animal testing for cardiac affect analyses, which are usually quite time-consuming and expensive. Thus, the functional tissue assay system is particularly useful in drug development and toxicity testing of any compound a human or animal might get in contact with. Microelectrode arrays (MEAs) are devices which allow the multiple extracellular recording of action potential generation and propagation within for example ES cell-derived cardiomyocytes. This recordings resemble the well-known ECG as it is used by physicians. The matrix of the MEAs usually consists of 60 gold electrodes integrated into the bottom of a specially designed cell culture device. ES cell-derived embryoid bodies (EBs) can be cultured in such devices. After attachment and spreading on the surface, the cells of the EBs containing the cardiomyocytes get in contact with the electrodes. All outcoming extracellular action potentials can then be recorded synchroneously during both short- and long time observation experiments. The following analysis of frequencies and latencies with an appropriate program allows to reveal the fine "electrical map" of the beating clusters.

For example, electrophysiological properties prior, during and after adding the test compound to cardiac myocytes can be followed by recordings of extracellular field potentials with microelectrode arrays (MEA) consisting of, e.g., 60 substrate-integrated electrodes; see Banach et al. Am. J. Physiol. Heart Circ. Physiol. 284 (2003), H2114-2123. Multiple arrays of tungsten microelectrodes were used to record the concurrent responses of brain stem neurons that contribute to respiratory motor pattern generation; see Morris et al., Respir. Physiol. 121 (2000), 119-133.

The above mentioned parameters may be used in the cell-based assay system of the present invention any one of said further parameters besides the measuring of electrical activity of said biological material through said electrode array.

Preferably, embryoid bodies are used in the assays of the present invention to test the chemical composition; see also infra. The choice of the particular species from which the embryoid body is derived will typically reflect a balance of several factors. First, depending on the purpose of the study, one or more species may be of particular interest. For example, human embryoid bodies will be of particular interest for use with compositions being tested as potential human therapeutics but also for toxicological tests for substances including industrial chemicals, while equine, feline, bovine, porcine, caprine, canine, or sheep embryoid bodies may be of more interest for a potential veterinary therapeutic. Embryoid bodies of other species commonly used in preclinical testing, such as guinea pigs, mice, rat, rabbits, pigs, and dogs, are also preferred. Typically, embryoid bodies of these species will be used for "first pass" screening, or where detailed information on toxicity in humans is not needed, or where a result in a murine or other one of these laboratory species has been correlated to a known toxicity or other effect in humans. Furthermore, with respect to human therapeutics, regulatory agencies generally require animal data before human trials can begin; it will generally be desirable to use embryoid bodies of species which will be used in the preclinical animal studies. The results of testing in the embryoid bodies can then guide the researcher on the degree and type of toxicity to anticipate during the animal trials. Certain animal species are known in the art to be better models of human toxicity of different types than are others, and species also differ in their ability to metabolize drugs; see, e.g., Williams, Environ. Health Perspect. 22 (1978), 133-138; Duncan, Adv. Sci. 23 (1967), 537-541. Thus, the particular species preferred for use in a particular preclinical toxicity study may vary according to the intended use of the drug candidate. For example, a species which provide a suitable model for a drug intended to affect the reproductive system may not be as suitable a model for a drug intended to affect the nervous system. Criteria for selecting appropriate species for preclinical testing are well known in the art.

Once an embryoid body culture has been initiated, it can be contacted with a chemical composition. Conveniently, the chemical composition is in an aqueous solution, preferably in a solvent conventionally used in cell culture, for example DMSO, and is introduced to the culture medium; see also the examples. The introduction can be by any convenient means, but will usually be by means of a pipette, a micropipettor, or a syringe. In some applications, such as high throughput screening, the chemical compositions will be introduced by automated means, such as automated pipetting systems, which may be on robotic arms. Chemical compositions can also be introduced into the medium as in powder or solid forms, with or without pharmaceutical excipients, binders, and other materials commonly used in pharmaceutical compositions, or with other carriers which might be employed in the intended use. For example, chemical compositions intended for use as agricultural chemicals or as petrochemical agents can be introduced into the medium by themselves to test the toxicity of those chemicals or agents, or introduced in combination with other materials with which they might be used or which might be found in the environment, to determine if the combination of the chemicals or agents has a synergistic effect. Typically, the cultures will be shaken at least briefly after introduction of a chemical composition to ensure the composition is dispersed throughout the medium.

The time as which a chemical composition is added to the culture is within the discretion of the practitioner and will vary with the particular study objective. Conveniently, the chemical composition will be added as soon as the embryoid body develops from the stem cells, permitting the determination of the alteration in protein or gene expression on the development of all the tissues of the embryoid body. It may be of interest, however, to focus the study on the effect of the composition on a particular tissue type. As previously noted, individual tissues, such as muscle, nervous, and hepatic tissue, are known to develop at specific times after the embryoid body has formed. Addition of the chemical composition can therefore be staged to occur at the time the tissue of interest commences developing, or at a chosen time after commencement of that development, in order to observe the effect on altering gene or protein expression in the tissue of interest.

Different amounts of a chemical composition will be used to contact an embryoid body depending on the amount of information known about the toxicity of that composition, the purposes of the study, the time available, and the resources of the practitioner. A chemical composition can be administered at just one concentration, particularly where other studies or past work or field experience with the compound have indicated that a particular concentration is the one which is most commonly found in the body. More commonly, the chemical composition will be added in different concentrations to cultures of embryoid bodies run in parallel, so that the effects of the concentration differences on gene or protein expression and, hence, the differences in toxicity of the composition at different concentrations, can be assessed. Typically, for example, the chemical composition will be added at a normal or medium concentration, and bracketed by twofold or fivefold increases and decreases in concentration, depending on the degree of precision desired.

Where the composition is one of unknown toxicity, a preliminary study is conveniently first performed to determine the concentration ranges at which the composition will be tested. A variety of procedures for determining concentration dosages are known in the art. One common procedure, for example, is to determine the dosage at which the agent is directly toxic. The practitioner then reduces the dose by one half and performs a dosing study, typically by administering the agent of interest at fivefold or twofold dilutions of concentration to parallel cultures of cells of the type of interest. For environmental contaminants, the composition will usually also be tested at the concentration at which it is found in the environment. For agricultural chemicals, such as pesticides which leave residues on foodstuffs, the agent will usually be tested at the concentration at which the residue is found, although it will likely be tested at other concentrations as well. Thus, the dilution of test compounds can be done by making in separated tubes a series of dilution of 50 or 100 fold concentrated compounds in DMSO. One or two μl of each dilution are distributed in each well before cell suspension distribution.

The above considerations with respect to contacting the compounds with the EBs, contacting time, etc, also apply to the assays of the invention performed on e.g. ES cells, tissue and non-human animals, if applicable.

In accordance with the assay system of the present invention, preferably any one or all of the following parameters are analyzed:
(i) $Na^+$ channels;
(ii) $Ca^{2+}/K^+$ channels;
(iii) $K^+$ channels;
(iv) Amplitude and/or Field potential duration (FDP),
(v) Chronotrophy of cardiac cells or burst periods of neuronal cells;
(vi) Arrhythmias, EAD like phenomena;
(vii) pH-value;
(viii) oxygen partial pressure ($pO_2$);
(ix) Beating arrest; and
(x) Analysis of AV-Dissociation contractility, NO-effects and/or morphological changes.

MEAs and methods for their use in analyses of biological cells are known to the person skilled in the art. For example, international application WO97/05922 describes a microelectrode arrangement for leaking, with local resolution, electrical cell potentials, or for electrical stimulation of networks of biological cells such as for example cell cultures, tissue slices "in vitro" or biological tissue "in vivo". A micro-element device such as described in international application WO98/22819 may be used, which has a plurality of microelements, which may be configured as microelectrodes, arranged on a substrate and adapted for making contact to cells present in a liquid environment. The cells are guided onto the microelectrodes, are isolated or are mechanically attracted to the microelectrodes. A negative-pressure force or a hydrodynamic force may be applied on the cells. In addition, the use of an electrode array as described in international application WO01/65251 may be adapted in accordance with the teaching of the present invention.

For analyses of the multielectrode data several tools available in the prior art may be used, see for example Egert et al., "MEA-tools: An open source toolbox for the analysis of multielectrode data with MATLAB. J. Neuroscience Methods 117 (2002), 33-42, and Banach et al., Am. J. Physiol. Heart Circ. Physiol. 284 (2003), H2114-2123).

In a preferred embodiment, the test sample comprises embryoid bodies (EBs) differentiated into cardiomyocytes, most preferably EBs that consist of functional cardiac tissue that beats autonomously and covers electrophysiological properties of atrial and ventricular cardiomyocytes, as well as of pacemaker cells.

The methods and assays described herein can replace various animal models, and form novel mammal-based tests and extreme environment biosensors. In particular, the methods of the invention can also be used for toxicological, mutagenic, and/or teratogenic in vitro tests. This is because people suffering from a disease are more vulnerable to intoxication and susceptible to side effects of pharmaceuticals, nutritions or any other compounds that one gets in contact with. Since the cells and tissue obtained in accordance with the present invention more closely resemble the in vivo situation the results obtained by the toxicological assays of the present invention are expected to correlate to in vivo toxicity of the tested compounds as well.

In a particular advantageous embodiment of the present invention, the above described assays are used as a system alternative for animal testing of cardiac effects of compounds, which is quite time consuming and expensive. This embodiment is based on "cardiobodies", i.e. embryoid bodies (EBs) differentiated into cardiomyocytes, preferably those described in international application WO2005/005621. Cardiobodies are preferably derived from mouse, rat or human embryonic stem cells. Cardiobodies consist of functional cardiac tissue that beats autonomously and covers electrophysiological properties of atrial and ventricular cardiomyocytes, as well as of pacemaker cells.

In a particular preferred embodiment, ES cells of the mouse cell line R1 (Nagy et al., Proc. Natl. Acad. Sci. 90 (1993), 8424-8428, available from the ATCC under accession no. SCRC-1011) or a cell line derived thereof are used in the assays of the present invention; see also Example 2.

In one embodiment, cardiobodies are plated on a multielectrode array system (MEA, MultiChannel Systems, Reutlingen, Germany). Recordings of extracellular field potentials with microelectrode arrays consisting of 60 substrate-integrated electrodes can be done as described for example in Banach et al., Am. J. Physiol. Heart Circ. Physiol. 284 (2003), H2114-2123. Extracellular recordings of the field potential reflect the electrophysiological changes during excitation of the cardiomyocytes in cardiobodies. In a particular preferred embodiment, automated analysis is performed using the AxioTools software developed by the Axiogenesis AG, Cologne, Germany.

In a particular preferred embodiment, the present invention relates to a method for screening a substance for the ability to ameliorate cardiomyopathy comprising:
(a) contacting a test sample comprising an in vitro differentiated cardiomyocyte as defined above with a test substance prior, during or after said cell is induced to display a predefined diseased phenotype which substantially corresponds to a phenotype of a diseased cell, tissue or organ;
(b) measuring a cardiomyopathic parameter in the cardiomyocyte of step (a);
(c) comparing the measurement obtained in step (b) to that of a cardiomyocyte not subjected to the substance;
wherein the measurement of the cardiomyopathic parameter in the cardiomyocytes of step (a) is consistent with a reduction in cardiac hypertrophy.

Characterization of cardiomyocytes can be done by various parameters known to those skilled in the art. For example, the cells can be characterized according to a number of phenotypic criteria. Cardiomyocytes often have morphological characteristics, for example they can be spindle, round, triangular or multi-angular shaped, with striations characteristic of sarcomeric structures detectable by immunostaining; see also FIG. 2. They may form myotube-like structures and show typical sarcomeres and atrial granules when examined by electron microscopy.

Under appropriate circumstances, stem cell-derived cardiomyocytes often show spontaneous periodic contractile activity. This means that when they are cultured in a suitable tissue culture environment with an appropriate $Ca^{2+}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between 6 and 200 contractions per minute, and often between 20 and 90 contractions per minute. Individual cells may show spontaneous periodic contractile activity on their own, or they may show spontaneous periodic contractile activity in concert with neighboring cells in a tissue, cell aggregate, or cultured cell mass.

The contractile activity of the cells can be characterized according to the influence of culture conditions on the nature and frequency of contractions. Compounds that reduce available $Ca^{2+}$ concentration or otherwise interfere with transmembrane transport of $Ca^{2+}$ often affect contractile activity. For example, the L-type calcium channel blocker diltiazem inhibits contractile activity in a dose-dependent manner.

On the other hand, adrenoceptor agonists like isoprenaline and phenylephrine have a positive chronotropic effect. Further characterization of functional properties of the cell can involve characterizing channels for $Na^+$, $K^+$, and $Ca^{2+}$. Electrophysiology can be studied by patch clamp analysis for cardiomyocyte like action potentials; see Igelmund et al., Pfluges Arch. 437 (1999), 669; Wobus et al., Ann. N.Y. Acad. Sci. 27 (1995), 752; and Doevendans et al., J. Mol. Cell Cardiol. 32 (2000), 839.

The cardiomyopathic parameter may be any one of those described hereinbefore and preferably is expression of a gene or activity of a gene product selected from the group consisting of an atrial natriuretic factor gene, a b-type natriuretic peptide gene, a β-myosin heavy chain gene, an α-skeletal actin gene, c-FOS, c-JUN, c-MYC, early growth response genes, heat shock protein 70, alpha-myosin heavy chain, collagen III, preproendothelin-1, myosin light chain 2, $Na^+/H^+$ exchanger, cardiac alpha-actin, $Na^+/Ca^{2+}$ exchanger, phosphatidylinositol-3 receptor, angiotensin-converting enzyme, collagen I, collagen XV, sarcoplasmic reticulum Ca-ATPase-2 alpha, beta-adrenoreceptor, protein kinase C, and phospholamban.

In one embodiment, a therapeutic of the invention can be assayed for activity in treating or preventing cardiac hypertrophy by contacting cultured cells that exhibit an indicator of a cardiac hypertrophy disease in vitro with the therapeutic; and comparing the level of said indicator in the cells contacted with the therapeutic, with said level of said indicator in cells not so contacted, wherein an altered level of such indicators in said contacted cells indicates that the therapeutic has activity in treating or preventing cardiac hypertrophy disease. Specific examples of such cardiac hypertrophy indicators include, but are not limited to: increased myocardial cell size (Simpson et al., J. Clin. Invest. 72 (1983), 732-738), an increase in the assemble of an individual contractile protein (MLC-2) into organized contractile units (Iwaki et al., J. Biol. Chem. 265 (1990), 13809-13817), accumulation of contractile proteins (Lee et al., J. Biol. Chem. 263 (1988), 7352-7358), increased protein content per cell (Lai et al., Am. J. Physiol. 271 (1996), H1197-H2208), activation of the [beta]-MHC gene and repression of the [alpha]-MHC gene (Lompre et al., Int. Rev. Cytol. 124 (1991), 137-186), transient upregulation of [alpha]-skeletal isoactin gene (Izumo et al., Proc. Natl. Acad. Sci. USA 85 (1988), 339-343); permanent reactivation of [alpha]-smooth actin isoform (Black et al., J. Clin. Invest. 88 (1991), 1581-1588), increased expression of myosin light chains 1 and 2 (Cummins, Biochem. J. 205 (1982), 195-204), transient activation of [beta]isoform of tropomyosin (Izumo et al., Proc. Natl. Acad. Sci. USA 85 (1988), 339-343), increased expression of fetal type isoenzymes (BB+MB) of creatine kinase and of the M-LDH isoform of lactate dehydrogenase (Ingwall et al., N. Engl. J. Med. 313 (1985), 1050-1054), accumulation of the fetal forms of cellular fibronectin in the wall of coronary arteries and in focal areas of the myocardium early after rat aortic stenosis (Samuel et al., J. Clin. Invest. 88 (1991), 1737-1746), transient upregulation of c-fos, c-myc, c-jun, junB, and nur 77 (Komuro et al., Circ. Res. 62 (1988), 1075-1079; Izumo et al., Proc. Natl. Acad. Sci. USA 85 (1988), 339-343; Rockman et al., Proc. Natl. Acad. Sci. USA 88 (1991), 8277-8281), a transient and early expression of three heat-shock proteins (HSP70, HSP68, and HSP58) (Delcayre et al, J. Clin. Invest. 82 (1988), 460-468), accumulation of mRNAs encoding transforming growth factor [beta]1 (TGF[beta]1), insulin like growth factor-I, and early growth response factor 1 (Egr-1), a serum-inducible zinc finger protein (Schneider and Parker, Mol. Biol. Med. 8 (1991), 167-183; Chien et al., FASEB J. 5 (1991), 3037-3046), the ventricular expression of atrial natriuretic factor (ANF) (Mercadier and Michael, In Swynghedauw B, ed. Research in Cardiac Hypertrophy and Failure. Paris, INSERM/John Libbey Eurotext (1990), 401-413), and the decreased expression of the slow skeletal/cardiac form SERCA2a isoform of the Ca ATPase of the sarcoplasmic reticulum (Komuro et al., J. Clin. Invest. 83 (1989), 1102-1108; Nagai et al., Proc. Natl. Acad. Sci. USA 86 (1989), 2966-2970; De la Bastie et al., Circ. Res. 66 (1990), 554-564; Mercadier et al., J. Clin. Invest. 85 (1990), 305-309).

The advantages of this particular embodiment of screening assays of the present invention over conventional in-vitro assays include

- Highly standardized cell culture model, homogeneous and reproducible production of CardioBodies;
- Presence of atrial, ventricular, and pacemaker cells with normal physiological behavior (e.g. expression and regulation of ion channels);
- ECG-like screening of all electrophysiological properties of the CardioBody including effects on all ion channels, chronotropy and appearance of arrhythmias;
- Entirely in vitro-based system, no requirement for laborious cell preparation
- Time- and cost-saving Thus, in the various assays of the present invention compounds, in particular cardiac active compounds can be tested in accordance with methods described in DE 195 25 285 A1; Seiler et al., ALTEX 19 Suppl 1 (2002), 55-63; Takahashi et al., Circulation 107 (2003), 1912-1916 and Schmidt et al., Int. J. Dev. Biol. 45 (2001), 421-429; the latter describing ES cell test (EST) used in a European Union validation study for screening of embryotoxic agents by determining concentration-dependently the differentiation of ES cells into cardiac and myogenic cells.

Cells and tissue of the CNS may also be analyzed using an electrode array as described above. Means and methods for analyzing regulatory interactions of neuronal activity of cells and tissue cultures on microelectrode arrays are known to the person skilled in the art; see for example van Bergen et al., Brain Res. Brain Res. Protocol 2003/11 (2003), 123-133 and international application WO01/65251. Similarly, cells and tissue related to the liver can be tested; see, e.g., US2003/0003573.

Preferred compound formulations for testing do not include additional components, such as preservatives, that have a significant effect on the overall formulation; see also supra. Thus preferred formulations consist essentially of a biologically active compound and a physiologically acceptable carrier, e.g. water, ethanol, DMSO, etc. However, if a compound is liquid without an excipient the formulation may consist essentially of the compound itself. Furthermore, a plurality of assays may be run in parallel with different compound concentrations to obtain a differential response to the various concentrations. As known in the art, determining the effective concentration of a compound typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection.

Compounds of interest encompass numerous chemical classes, though typically they are organic molecules; see also supra. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Compounds and candidate agents are obtained from a wide variety of sources including libraries of synthetic or natural compounds; see also supra. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. For example, inhibition of tumor-induced angiogenesis and matrix-metalloproteinase expression in confrontation cultures of embryoid bodies and tumor spheroids by plant ingredients used in traditional Chinese medicine has been described by Wartenberg et al. in Lab. Invest. 83 (2003), 87-98.

Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The compounds may also be included in a sample including fluids to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Test compounds include all of the classes of molecules described above, and may further comprise samples of unknown content. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest compounds being assessed for potential therapeutic value, i.e. drug candidates.

The test compound may optionally be a combinatorial library for screening a plurality of compounds. Such a collection of test substances can have a diversity of about $10^3$ to about $10^5$ is successively reduced in running the method, optionally combined with others twice or more. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki et al., Bio/Technology 3 (1985), 1008-1012, allele-specific oligonucleotide (ASO) probe analysis (Conner et al., Proc. Natl. Acad. Sci. USA 80 (1983), 278), oligonucleotide ligation assays (OLAs) (Landegren et al., Science 241 (1988), 1077), and the like. Molecular techniques for DNA analysis have been reviewed (Landegren et al., Science 242 (1988), 229-237). Hence, the method of the present invention can also be used for transcriptional profiling of the in vitro differentiated cell; see, e.g., Ramalho-Santos et al., Science 298 (2002), 597-600; Tanaka et al., Genome Res. 12 (2002), 1921-1928.

The cell-based assay of the present invention is particularly suited to provide modulation reference patterns and databases of modulation reference patterns for a wide range of biologically active compounds. The reference patterns are then used for the identification and classification of test compounds. Evaluation of test compounds may be used to achieve different results.

Methods for the classification of biological agents according to the spectral density signature of evoked changes in cellular electric potential are known to the person skilled in the art; see, e.g., U.S. Pat. No. 6,377,057. Thus, biologically active compounds are classified according to their effect on ion channels, changes in membrane potential and ionic currents, and the frequency content of action potentials that the compound(s) evoke in excitable cells. The spectral density changes of such evoked membrane potential or action potential are a characteristic for each channel type that is modulated by the test compound. A pattern of spectral changes in membrane potential is determined by contacting a responsive cell with a compound, and monitoring the membrane potential or ionic currents over time. These changes correlate with the effect of that compound, or class of compounds, on the ion channels of the responding cell. This pattern of spectral changes provides a unique signature for the compound, and provides a useful method for characterization of channel modulating agents. The effect of a compound on ion channels, and on the action potential of a living cell, can provide useful information about the classification and identity of the compound. Methods and means for extracting such information are of particular interest for the analysis of biologically active compounds, with specific applications in pharmaceutical screening, drug discovery, environmental monitoring, biowarfare detection and classification, and the like. Examples of whole cell-based biosensors are described in Gross et al., Biosensors and Bioelectronics 10 (1995), 553-567; Hickman et al. Abstracts of Papers American Chemical Society 207 (1994), BTEC 76; and Israel et al. American Journal of Physiology: Heart and Circulatory Physiology 27 (1990), H1906-H1917.

Connolly et al., Biosens. Biores. 5 (1990), 223-234 describe a planar array of microelectrodes developed for monitoring the electrical activity of cells in culture. The device allows the incorporation of surface topographical features in an insulating layer above the electrodes. Semiconductor technology is employed for the fabrication of the gold electrodes and for the deposition and patterning of an insulating layer of silicon nitride. The electrodes were tested using a cardiac cell culture of chick embryo myocytes, and the physical beating of the cultured cells correlated with the simultaneous extracellular voltage measurements obtained. The molecular control of cardiac ion channels is reviewed by Clapham, Heart Vessels Suppl. 12 (1997), 168-169. Oberg and Samuelsson, J. Electrocardiol. 14 (1981), 13942, perform Fourier analysis on the repolarization phases of cardiac action potentials. Rasmussen et al. American Journal of Physiology 259 (1990), H370-H389, describe a mathematical model of electrophysiological activity in bullfrog atria.

A large body of literature exists in the general area of ion channels. A review of the literature may be found in the series of books, "The Ion Channel Factsbook", volumes 1-4, by Edward C. Conley and William J. Brammar, Academic Press. An overview is provided of: extracellular ligand-gated ion channels (ISBN: 0121844501), intracellular ligand-gated channels (ISBN: 012184451X), inward rectifier and intercellular channels (ISBN: 0121844528), and voltage gated channels (ISBN: 0121844536). Hille, B. (1992) "Ionic Channels of Excitable Membranes", 2.sup.nd Ed. Sunderland MA:Sinauer Associates, also reviews potassium channels.

In one example, the cells are coupled with a substrate such that electrophysiological changes in the cells in response to external stimuli can be measured, e.g., for use as a high-throughput screen for bioactive substances. The cells can also be transfected with DNA that targets, expresses, or knocks-out specific genes or gene products in the cell. By providing such chip-mounted cells coupled with measuring devices, such as a computer, many compounds can be screened rapidly and accurately. The cells or chips could also be coupled to the measuring device in arrays for large-scale parallel screening.

The assay methods of the present invention can be in conventional laboratory format or adapted for high throughput. The term "high throughput" (HTS) refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired.

In another preferred embodiment, the method of the present invention comprises taking 2, 3, 4, 5, 7, 10 or more measurements, optionally at different positions within the array. Several test substances can be combined and either added simultaneously or sequentially to gain information about possible enhancing or quenching effects. Thus a further aspect of the invention relates to the method described previously, wherein said contacting step further includes contacting said test sample with at least one second test substance in the presence of said first test substance. Two or more substances tested in combination will provide information about their interaction in general. In one embodiment of the screening methods of the present invention a compound known to activate or inhibit disease process is added to the sample or culture medium.

Furthermore, the above-described methods can, of course, be combined with one or more steps of any of the above-described screening methods or other screening methods well known in the art. Methods for clinical compound discovery comprises for example ultrahigh-throughput screening (Sundberg, Curr. Opin. Biotechnol. 11 (2000), 47-53) for lead identification, and structure-based drug design (Verlinde and Hol, Structure 2 (1994), 577-587) and combinatorial chemistry (Salemme et al., Structure 15 (1997), 319-324) for lead optimization. Once a drug has been selected, the method can have the additional step of repeating the method used to perform rational drug design using the modified drug and to assess whether said modified drug displays better affinity according to for example interaction/energy analysis. The method of the present invention may be repeated one or more times such that the diversity of said collection of compounds is successively reduced.

Substances are metabolized after their in vivo administration in order to be eliminated either by excretion or by metabolism to one or more active or inactive metabolites (Meyer, J. Pharmacokinet. Biopharm. 24 (1996), 449-459).

Thus, rather than using the actual compound or drug identified and obtained in accordance with the methods of the present invention a corresponding formulation as a pro-drug can be used which is converted into its active form in the patient by his/her metabolism. Precautionary measures that may be taken for the application of pro-drugs and drugs are described in the literature; see, for review, Ozama, J. Toxicol. Sci. 21 (1996), 323-329.

Furthermore, the present invention relates to the use of a compound identified, isolated and/or produced by any of these methods for the preparation of a composition for the treatment of disorders related to, for example damaged tissue or aberrant tissue or organ formation, heart insufficiency, etc.; see also supra. Preferably, the isolated compound or corresponding drug is useful for the treatment of a cardiomyopathy. As a method for treatment the identified substance or the composition containing it can be administered to a subject suffering from such a disorder. Compounds identified, isolated and/or produced by the method described above can also be used as lead compounds in drug discovery and preparation of drugs or prodrugs. This usually involves modifying the lead compound or a derivative thereof or an isolated compound as described hereinbefore such as modifying said substance to alter, eliminate and/or derivatize a portion thereof suspected causing toxicity, increasing bioavailability, solubility and/or half-life. The method may further comprise mixing the substance isolated or modified with a pharmaceutically acceptable carrier. The various steps recited above are generally known in the art. For example, computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, peptidomimetics and/or computer aided design of appropriate derivatives and analogues can be used, for example, according to the methods described above. Methods for the lead generation in drug discovery also include using proteins and detection methods such as mass spectrometry (Cheng et al. J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931). They may also include or rely on quantitative structure-action relationship (QSAR) analyses (Kubinyi, J. Med. Chem. 41 (1993), 2553-2564, Kubinyi, Pharm. Unserer Zeit 23 (1994), 281-290) combinatorial biochemistry, classical chemistry and others (see, for example, Holzgrabe and Bechtold, Pharm. Acta Helv. 74 (2000), 149-155). Furthermore, examples of carriers and methods of formulation may be found in Remington's Pharmaceutical Sciences.

Once a drug has been selected in accordance with any one of the above-described methods of the present invention, the drug or a pro-drug thereof can be synthesized in a therapeutically effective amount. As used herein, the term "therapeutically effective amount" means the total amount of the drug or pro-drug that is sufficient to show a meaningful patient benefit, i.e., treatment, healing, prevention or amelioration of damaged tissue, or an increase in rate of treatment, healing, prevention or amelioration of such conditions. In addition or alternatively, in particular with respect to pre-clinical testing of the drug the term "therapeutically effective amount" includes the total amount of the drug or pro-drug that is sufficient to elicit a physiological response in a non-human animal test.

In one embodiment, the method of the invention further comprises mixing the substance isolated or modified with a pharmaceutically acceptable carrier. Examples of carriers and methods of formulation may be found in Remington's Pharmaceutical Sciences.

The present invention also relates to kit compositions containing specific reagents such as those described herein-before useful for conducting any one of the above described methods of the present invention, containing the vector or the composition of vectors described hereinbefore, multi- or pluripotent cells, and optionally culture medium, recombinant nucleic acid molecules, physiologically active agents, standard compounds, etc. Such a kit would typically comprise a compartmentalized carrier suitable to hold in close confinement at least one container. The carrier would further comprise reagents useful for performing said methods. The carrier may also contain a means for detection such as labeled enzyme substrates or the like. Instructions can be provided to detail the use of the components of the kit, such as written instructions, video presentations, or instructions in a format that can be opened on a computer (e.g. a diskette or CD-ROM disk). These instructions indicate, for example, how to use the cells to screen test agents of interest (such as inotropic drugs).

In addition, the present invention relates to an apparatus and array, respectively, for use in the methods and assays of the present invention described herein. For example, a cell-potential measurement apparatus having a plurality of microelectrodes and which may be used and/or adapted in accordance with the teaching of the present invention is described in European patent application EP 0 689 051 A3.

Furthermore, international application WO98/54294 describes an apparatus and method for monitoring cells and a method for monitoring changes in cells upon addition of an analyte to the cell's environment, comprising a device which includes an array of microelectrodes disposed in a cell culture chamber, upon which array a portion of cells adhere to the surfaces of the microelectrodes. The diameter of the cells are larger than the diameters of the microelectrodes. A voltage signal is applied across each of the microelectrodes and a reference electrode. Detection and monitoring of the signals resulting from the application of the voltage signal provides information regarding the electrical characteristics of the individual cells, including impedance (combined cell membrane capacitance and conductance), action potential parameters, cell membrane capacitance, cell membrane conductance, and cell/substrate seal resistance.

Further means and methods that may be implemented in accordance with the teaching of the present invention can be found in the literature, see for example Egert et al., Brain Res. Brain Res. Protoc. 2 (1998), 229-242; Duport et al., Biosens. Bioelectron. 14 (1999), 369-376 and German patent application DE 195 29 371 A1.

As has already been discussed in context with the assay system of the present invention for screening putative drugs, the observations made in accordance with the present invention can also be applied to establish a novel method of identifying putative target genes for therapeutic intervention within the treatment of a given disease. Therefore, in a further aspect the present invention relates to a method of identifying and/or obtaining a gene or gene product involved in a disease as a drug target comprising expression profiling of an in vitro differentiated cell as defined above before and after induction of said phenotype, wherein the differential expression of a gene or gene product is indicative for a potential drug target, and optionally comprising cloning the identified gene or a corresponding cDNA or fragment thereof. The diseased phenotype can be induced for example by adding a physiogically active compound as described above. Techniques for assaying differential expression are well known to the person skilled in the art; see also the references cited herein. Likewise, the cloning of the identified sequences can be done according to standard methods such as described in Sambrook et al. and others; see also supra.

Hence, the in vitro differentiated cells of this invention are also of interest in identifying expression patterns of transcripts and newly synthesized proteins that are characteristic for a disease state. Expression patterns of the differentiated cells are obtained and compared with control cell lines, such as differentiated cells, which have been treated so as to induce the disease phenotype. The use of microarray in analyzing gene expression is reviewed generally by Fritz et al., Science 288 (2000), 316; Microarray Biochip Technology, www-.Gene-Chips.com. An exemplary method is conducted using a Genetic Microsystems array generator, and an Axon Gene-Pix Scanner. Microarrays are prepared by first amplifying cDNA fragments encoding marker sequences to be analyzed, and spotted directly onto glass slides To compare mRNA preparations from two cells of interest, one preparation is converted into Cy3-labeled cDNA, while the other is converted into Cy5-labeled cDNA. The two cDNA preparations are hybridized simultaneously to the microarray slide, and then washed to eliminate non-specific binding. The slide is then scanned at wavelengths appropriate for each of the labels, the resulting fluorescence is quantified, and the results are formatted to give an indication of the relative abundance of mRNA for each marker on the array. Furthermore, subtractive suppression hybridization (SSH) can be used. SSH assay and uses thereof are described for example in international application WO03/093501. In particular, methods of identifying and isolating nucleic acid sequences, which are unique for a certain cell, tissue or organism are provided, wherein said unique nucleic acid sequences are related to for example diseased genes. Description how to perform subtractive suppression hybridization is also described in Diatchenko et al., Proc. Natl. Acad. Sci. USA 93 (1996), 6025-6030; Diatchenko et al., Meth. Enzym. 303 (1999), 349-380; and international application WO96/23079.

From the above, it is also apparent that the method of the present invention can be adapted to validate a potential drug target, for example by inducing the expression of a target gene in the in vitro differentiated cell during the induction of the diseased phenotype and monitoring whether the expression of the target gene suppresses or enhances the progression of the disease. Hence, in a further aspect the present invention relates to a method of validating a potential drug target comprising (a) altering the expression of a target a gene and/or activity of the target gene product in an in vitro differentiated cell as described above prior, during or after said cell is induced to display a predefined diseased phenotype which substantially corresponds to a phenotype of a diseased cell, tissue or organ; and (b) determining a responsive change of the phenotype of said cell, wherein a responsive change (i) preventing or delaying the onset or the progression of the diseased phenotype is indicative for a drug target to be activated, and (ii) enhancing the onset or progression the diseased phenotype is indicative for a drug target to be inhibited for the treatment of the disease.

This aspect of the present invention is particularly useful for determining synergistic effects of components in multifactoral diseases, for example diseases which are determined by mutations in several genes and/or are based on genetic predisposition as well as environmental factors.

Yet another aspect of the present invention relates to a method of conducting a drug discovery business, comprising:
providing one or more assay systems or components thereof as described herein for identifying a drug candidate; and/or
conducting therapeutic profiling of drugs identified in the previous step, or further analogs thereof, for efficacy and toxicity according to the assays of the present invention; and
formulating a pharmaceutical preparation including one or more drugs identified in the previous step as having an acceptable therapeutic profile.

Utilizing the methods described above, the identity of a drug can be determined. Agents are identified by their ability to alter the certain parameters such as those described hereinbefore, e.g. those described for MEAs. For suitable lead compounds that are identified, further therapeutic profiling of the agent, or analogs thereof, can be carried out for assessing efficacy and toxicity in animals. Those compounds having therapeutic profiles after animal testing can be formulated into pharmaceutical preparations for use in humans or for veterinary uses. The subject business method can include an additional step of establishing a distribution system for distributing the pharmaceutical preparation for sale, and may optionally include establishing a sales group for marketing the pharmaceutical preparation.

Instead of developing the identified drug in house, further drug development can also be achieved by a different company. Thus a further aspect of the present invention relates to a method of conducting a target discovery business comprising:
providing one or more assay systems described herein or components thereof for identifying a drug;
alternatively or in addition conducting therapeutic profiling of drugs for efficacy and toxicity according to the assays of the present invention; and
licensing, to a third party, the rights for further drug development and/or sales for drugs identified or profiled, or analogs thereof.

For suitable lead compounds that have been identified, further profiling of the agent, or further analogs thereof, can be carried out for assessing efficacy and toxicity in animals, depending on the modalities of the agreement with the respective third party. Further development of those compounds for use in humans or for veterinary uses will then be conducted by the third party. The subject business method will usually involve either the sale or licensing of the rights to develop said compound but may also be conducted as a service, offered to drug developing companies for a fee.

The present invention also relates to drugs identified according to the methods and assays described above as well as to pharmaceutical compositions for use in therapy comprising such a drug. The drug according to the invention can be combined with suitable diluents or carriers, preferably those which are pharmaceutically acceptable. Examples of such carriers, diluents and methods of formulation may be found in Remington's Pharmaceutical Sciences. To form a pharmaceutically acceptable composition suitable for effective administration, such compositions will contain an effective amount of the modulator. Carriers or diluents are usually sterile and non-toxic, and defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like. A therapeutically effective dose refers to that amount of modulator which is sufficient to achieve the desired effect on differentiation of target cells.

Further examples of suitable pharmaceutical carriers are well known in the art and include phosphate buffered saline solutions, emulsions, such as oil/water emulsions, various types of wetting agents, sterile solutions etc. Compositions comprising such carriers can be formulated by well known conventional methods. Accordingly, the present invention also provides a method of making a pharmaceutical composition for use in modulating cell differentiation comprising mixing a modulator of cell differentiation identified according to a method of the invention with a suitable diluent or carrier.

The appropriate concentration of the therapeutic agent might be dependent on the particular agent. The therapeutically effective dose has to be compared with the toxic concentrations; the clearance rate as well as the metabolic products play a role as do the solubility and the formulation. Therapeutic efficacy and toxicity of compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

In a preferred embodiment, therapeutics of the invention are administered therapeutically, and preferably, prophylactically, to patients suffering from or in danger of suffering from cardiac hypertrophy disease, preferably pressure overload cardiac hypertrophy, have previously suffered a systematic hypertension or aortic stenosis event, or exhibit one or more "risk factors" for cardiac hypertrophy (i.e., a characteristic, behavior or disorder correlated with increased incidence of cardiac hypertrophy) or one or more conditions associated with cardiac hypertrophy; see Hutter, "Congestive Heart Failure", in Scientific American: Medicine, Volume 1(1:II), eds. Dale and Federman (Scientific American, Inc. 1994) and "Hypertrophic Cardiomyopathy", in The Merck Manual of Diagnosis and Therapy, Chapter 27, 519-522, eds. Berkow et al. (Merck Sharp & Dohme Research Laboratories 1987).

Major indications of predisposition for cardiac hypertrophy predisposition are chest pains, syncope, palpitations, effort dyspnea or symptoms of aortic stenosis or coronary artery disease, or any combination the foregoing indications. Chest pain is usually typical angina related to exertion. Syncope is usually exertional, due to a combination of arrhythmia, outflow tract obstruction, and diastolic filling of the ventricle. Dyspnea on exertion is a result of poor diastolic compliance of the left ventricle that leads to rapid rise in LVEDP as flow increases. Palpitations are produced by ventricle or atrial arrhythmias.

Patients suffering from heart failure may also be predisposed to cardiac hypertrophy. By way of example but not by way of limitation, coronary artery disease, cardiomyopathy, myocarditis, aortic stenosis, hypertension, coarctation of the aorta, aortic regurgitation, mitral regurgitation, left-to-right shunts, restrictive cardiomyopathy, ischeric heart disease, pericardial tamponade, constrictive pericarditis, or restrictive cardiomyopathy can increase the likelihood that a patient will suffer a cardiac hypertrophy.

Therapeutics of the invention may also be administered with drugs which treat or ameliorate the effect of certain risk factors for cardiac hypertrophy. In a preferred embodiment, a therapeutic of the invention is administered with one or more anti-cardiac-hypertrophydrug such as, but not limited to, [beta]-Adrenoceptor blockers and Ca-channel blockers, or carried out in conjunction with anti-arrhythmic therapy, antibiotic prophylaxis, or surgical treatment in the form of septal myotomy, myormectomy, or mitral valve replacement.

It is within the skill of those in the art to monitor and adjust the treatment or prophylactic regimen for treating or preventing cardiac hypertrophy disease while treating or preventing other potentially associated diseases or disorders, such as systematic hypertension.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete under-standing can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds.

1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11 (2001), 98-107.

Example 1

Generation of Hypertrophic Cardiomyocytes from Embryonic Stem Cells

At present cardiomyocytes prepared from rodent hearts are used as the standard in vitro model to study hypertrophic cardiomyocytes at the molecular level (Chlopcikova et al., Biomed. Pap. Med. Fac. Univ. Palacky Olomouc Czech. Repub. 145 (2001), 49-55). These cells display upon stimulation numerous features of hypertrophic cardiomyocytes in vivo (Chien et al., FASEB J. 5 (1991, 3037-3046). Various substances can be used as hypertrophic stimuli in this system, including endothelins (Shubeita et al., J. Biol. Chem. 265 (1990), 20555-20562; Suzuki et al., FEBS Lett. 268 (1990), 149-151; Ito et al., Circ. Res. 69 (1991), 209-215), 1-adrenergic agonists (Simpson, Circ. Res. 56 (1985), 884-894; Meidell et al., Am. J. Physiol. 251 (1986), H1076-H1084; Henrich and Simpson, J. Mol. Cell. Cardiol. 20 (1988), 1081-1085); and Angiotensin II (Sadoshima and Izumo, Circulation Research 73 (1993), 413-423). Also mechanical stimuli can induce a hypertrophic phenotype in this model (Komuro et al., J. Biol. Chem. 265 (1990), 3595-3598; Sadoshima et al., J. Biol. Chem. 267 (1992), 10551-10560).

Hypertrophic cardiomyocytes in that cell culture system are characterized by increased size, increased protein synthesis, increase in sarcomeric assembly and reexpression of a fetal gene program, e.g. enhanced expression of the ANF (atrial natriuretic factor) gene. In order to test if embryonic stem (ES) cell-derived cardiomyocytes display similar features upon stimulation, the following experiments were performed. Green fluorescent cardiomyocytes were generated in accordance with the teachings of in international applications WO99/01552 and WO02/051987 in the following way. ES cells (line D3, ATCC, CRL 1934) that were transfected with a bi-cistronic vector containing the genes for green fluorescent protein (GFP) and puromycin-resistance under the transcriptional control of the 2-myosin heavy chain promoter (see WO02/051987), were induced to form aggregates (embryonic bodies, EBs) in the absence of LIF either according to the method in WO99/01552 and WO02/051987, respectively, or as described in European patent application no. 03015401.7. EBs were cultured for 9 days in IMDM (Invitrogen) supplemented with 20% FCS (Invitrogen, batch controlled) at 37° C., 5% $CO_2$ and 95% humidity on 10 cm bacteriological dishes (Greiner). Subsequently, puromycin (Sigma, 2.5 g/ml) was added to the cell culture medium and cells were cultured for further 10 days. Cells were then transferred to a layer of inactivated mouse embryonic fibroblasts in a 24-well plate (Costar) and cultured for two days, in the absence of puromycin (IMDM, 20% FCS). After two days, serum containing medium was replaced by serum-free medium (Medium 199, Invitrogen). After 24 h serum starvation cells were stimulated for 24 h by addition of endothelin-1 (100 nM, Sigma) or phenylephrine (200 µM, Sigma).

Figure 1B:
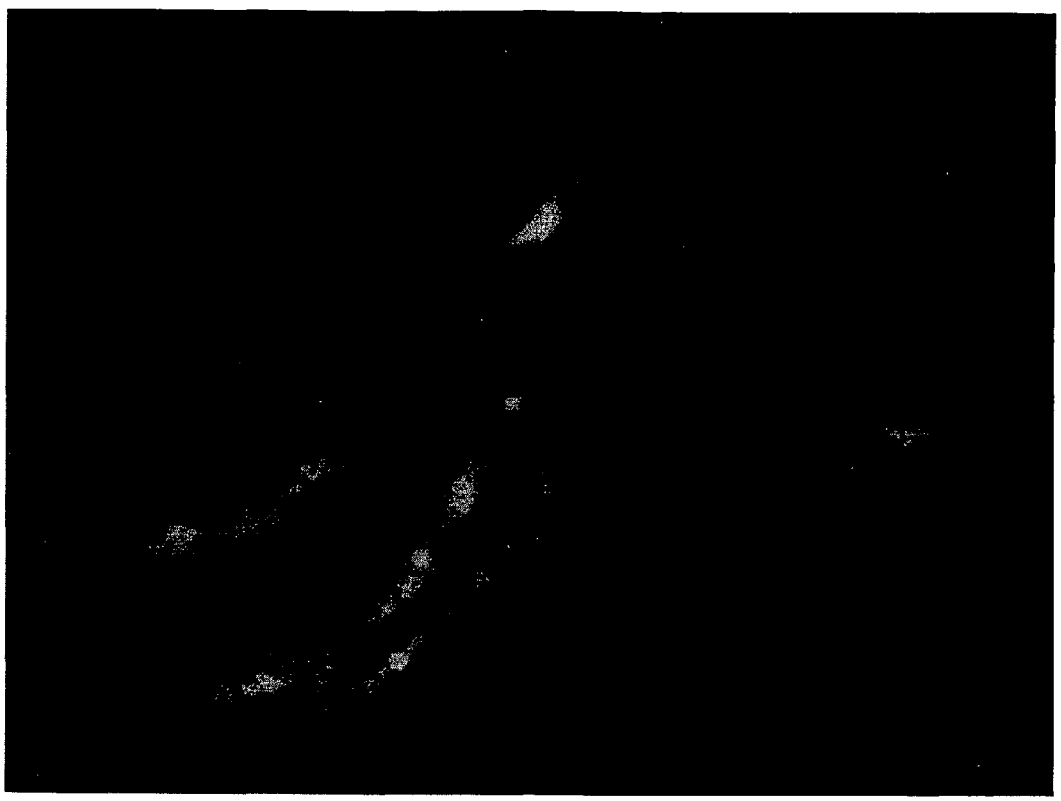
Figure 1C:
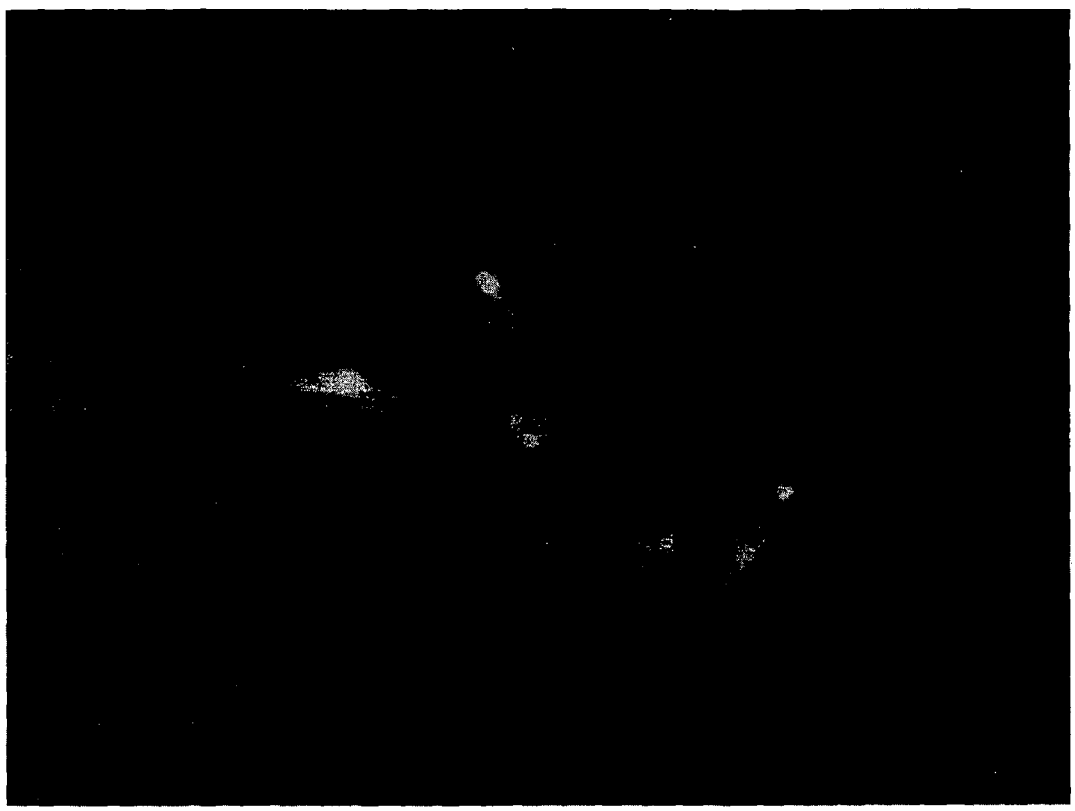
Figure 2A:
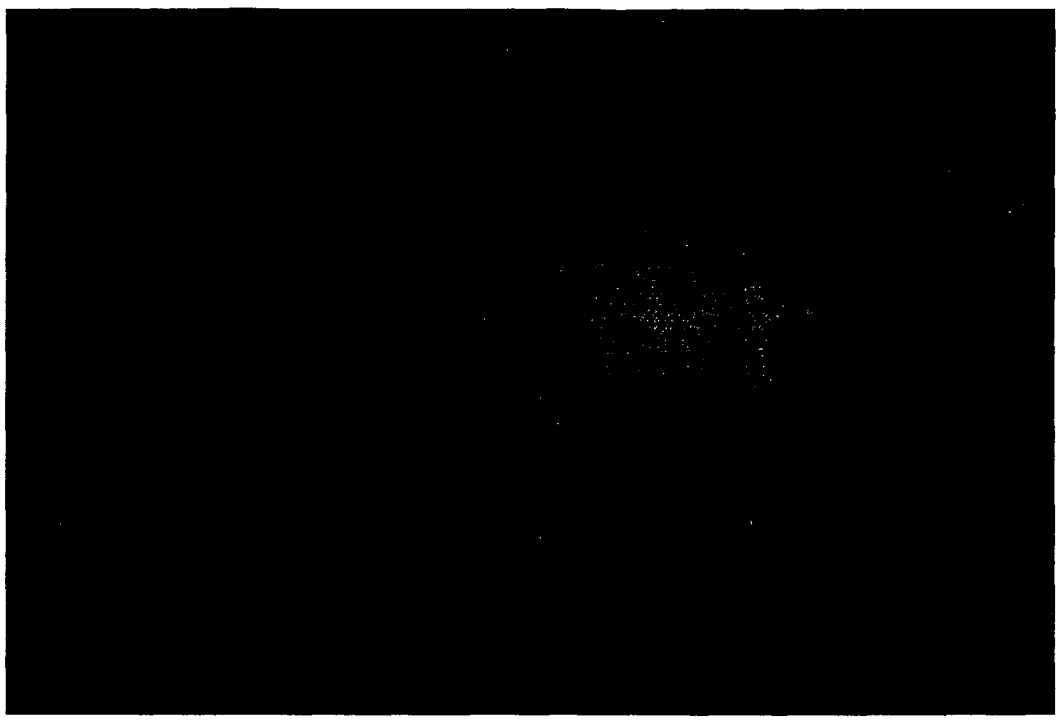
FIG. 2: Sarcomer organization of ES cell-derived cardiomyocytes upon stimulation by endothelin-1 and phenylephrine. Cardiomyocytes were cultured on inactive embryonic mouse fibroblasts and serum-starved for 24 h. Subsequently, cultures were stimulated for 24 h by phenylephrine (A; 200 µM) or endothelin-1 (B; 100 nM). C; untreated cells. Immunostaining of sarcomeric alpha-actinin.
Figure 2B:
Figure 2C:

As demonstrated in FIG. 1, ES cell-derived cardiomyocytes increase in size upon stimulation by endothelin-1 or phenylephrine. Immunostaining for sarcomeric—actinin (clone EA-53, Sigma) reveals that these stimuli lead to an increase in sarcomeric organization (FIG. 2). Thus, the ES cell-derived cardiomyocytes react to these stimuli in a similar way as described for rodent cardiomyocytes obtained from heart preparations (e.g. Yanazume et al., Mol. Cell Biol. 23 (2003), 3593-3606; Vara et al., J. Biol. Chem. 278 (2003), 21388-21394; Pikkarainen et al., J. Biol. Chem. 278 (2003), 3969-3975; Molkentin et al., Cell 93 (1998), 215-228).

In a further experiment, the possible induction of an early embryonic gene program upon stimulation by endohelin-1, angiotensin II, or phenylephrine was analysed. To this end, puromycin resistant ES cell-derived cardiomyocytes were obtained as described above; however, after the final 9 days in puromycin containing medium cells were not transferred to a feeder layer but were kept in suspension culture. Following serum-starvation for 24 h by cultivation in Medium 199, cells were stimulated for 24 h by addition of endothelin-1, phenyleprine, or angiotensin II (Sigma). RNA was extracted and reverse transcribed using standard methods.

Expression of ANF and brain natriuretic peptide (BNP) was analysed by PCR amplification of the respective cDNAs.

Figure 3:
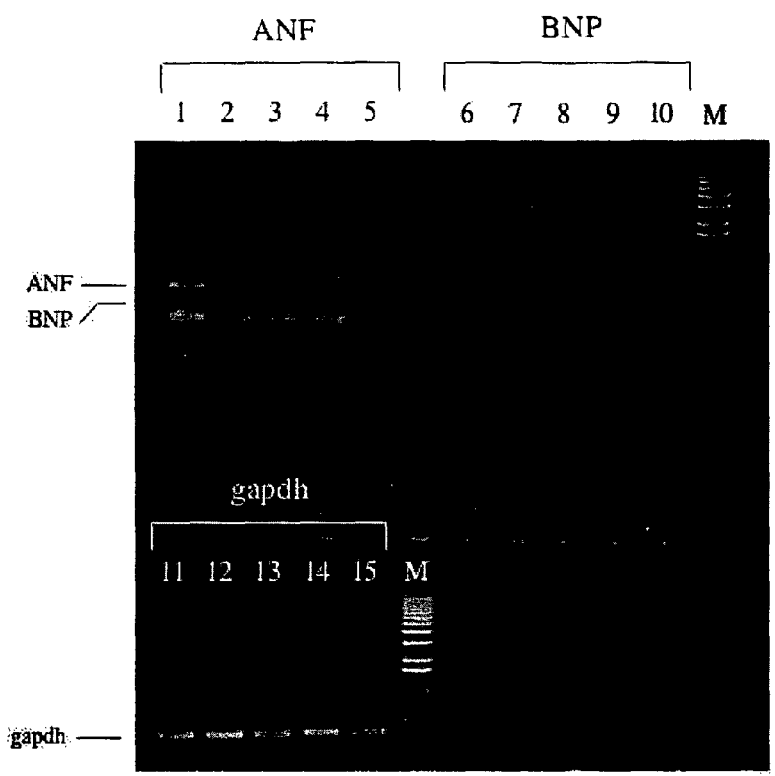
FIG. 3: Induction of ANF and BNP expression in ES cell-derived cardiomyocytes. Cardiomyocytes differentiated from ES cells were serum-starved for 24 h and subsequently stimulated by endothelin-1 (100 nM; lanes 1, 6, 11), phenylephrine (200 µM; lanes 2, 7, 11) or Angiotensin II (100 nM; lanes 3, 8, 13). Non-stimulated controls were cultured in serum-free medium (lanes 4, 9, 14) or serum-supplemented medium (lanes 5, 10, 15). Subsequently, RNA was extracted and cDNA was synthesized using random hexamer priming. ANF, BNP, and gapdh cDNAs were amplified and PCR products were analyzed by agarose gel electrophoresis. M, size marker. Amplification parameters were as follows. cDNAs were amplified for 32 (ANF and BNP) or 26 (gapdh) PCR cycles consisting each of 1 min at 94° C., 1 min at 56° C., and 1 min at 72° C. The following primers were used: ANF-5',5'-CTCCTTCTCCATCACCCTG-3' (SEQ ID NO: 14); ANF-3', 5'-TTTCCTCCTTGGCTGTTATC-3' (SEQ ID NO: 15); BNP-5', 5'-CAGCTCTTGAAGGACCAAGG-3' (SEQ ID NO: 18); BNP-3', 5'-AGACCCAGGCAGAGTCAGAA-3' (SEQ ID NO: 19); gapdh-5', 5'-GTGTTCCTACCCCCAAT-GTG-3' (SEQ ID NO: 16); gapdh-3', 5'-CTTGCTCAGT-GTCCTTGCTG-3' (SEQ ID NO: 17). Expected PCR product sizes were 468 bp (ANF), 242 bp (BNP), and 349 bp (gapdh).

FIG. 3 demonstrates that cells stimulated by endothelin-1 or phenylephrine show increased ANF and BNP expression compared to control. Angiotensin II stimulation leads to a modest increase in ANF and BNP expression. Increased ANF and BNP expression is a hallmark of hypertrophic cardiomyocytes and has been observed also in endothelin-1, angiotensin II and phenylephrine treated cardiomyocytes from rodent heart preparations (Day et al., Hypertension 9 (1987), 485-491; Saito et al., J. Clin. Invest. 83 (1989), 298-305; Kawakami et al., Clin. Sci. 90 (1996), 197-204; Cameron and Ellmers, Endocrinology 144 (2003), 2191-2194).

In summary, the experiments described in this section demonstrate that ES cell-derived cardiomyocytes display features similar to cardiomyocytes from rodent heart preparations with respect to stimulation by endothelin-1, angiotensin II, and phenylephrine.

Example 2

Up-Regulation of ANF Expression in Mouse ES Cell-Derived Cardiomyocytes Transgenic for Constitutively Active Calcineurin Cardiac hypertrophy is an adaptive response of the heart to different stimuli and is accompanied by a variety of changes of the cardiomyocytes at the molecular level. Studies analyzing the features of this process have shown $Ca^{2+}$ to play a central role, and thus proteins involved in the regulation of $Ca^{2+}$ homeostasis or proteins regulated by $Ca^{2+}$ are thought to play a critical role in the hypertrophic response (reviewed in McLennan, Eur. J. Biochem. 267 (2000), 5291-5297; Frey et al., Nat. Med. 6 (2000), 1221-1227). One protein involved in connecting $Ca^{2+}$ fluctuations and altered gene regulation is the $Ca^{2+}$-calmodulin-dependent protein phosphatase-2B, calcineurin (reviewed in Rao et al., Annu. Rev. Immunol. 15 (1997), 707-747). An elevation in intracellular calcium increases the activation of calcineurin, which in its activated form dephosphorylates the nuclear factor of activated T-cells (NFAT), thereby activating it (Okamura et al., Mol. Cell 6 (2000), 539-550; reviewed in Crabtree, J. Biol. Chem. 276 (2001), 2313-2316). A direct connection between calcineurin and cardiac hypertrophy was shown in transgenic mice expressing an activated form of calcineurin. These mice develop cardiac hypertrophy and heart failure mimicking human heart disease (Molkentin et al., Cell 93 (1998), 215-228). Genetically modified cardiomyocytes for in vitro studies may be obtained either from a correspondingly modified animal, or by genetic manipulation of primary cardiomyocytes. Both methods are time and cost consuming. Therefore, in accordance with the present invention it was aimed at generating cardiomyocytes expressing activated calcineurin in vitro directly from transgenic ES cells. To this end, a transgenic ES cell line containing a gene for a constitutively active form of calcineurin A catalytic subunit (O'Keefe et al., Nature 357 (1992), 692-694) under the control of the cardiomyocyte specific MHC promoter was generated. First, the MHC-pcDNA3 vector was generated by replacing the CMV promoter between the NruI-BamHI site in the pcDNA3 vector (Invitrogen) by the MHC promoter (Genebank: U71441). To obtain a cDNA encoding constitutively active calcineurin, RNA was extracted from adult mouse heart and used for cDNA generation using TRIzol reagent (Invitrogen) and SuperscriptTMII RNaseH-Reverse Transcriptase (Invitrogen), respectively, according to the manufacturers' protocol. The sequence encoding the constitutively active calcineurin A catalytic subunit lacking the C-terminal autoinhibitory domain, which corresponds to aal-398 (O'Keefe et al., Nature 357 (1992), 692-694), was amplified by PCR from total mouse heart cDNA. Primers used for amplification were 5-GGACTAGTCCAGCCACCATGTCCGAGC-CCAAGGC-3' (SEQ ID NO: 1) and 5'-ATAAGAATGCG-GCCGCTAAACTATTCAGTTTCTGAT-GACTTCCTTCCGG-3' (SEQ ID NO: 2), which harbor a SpeI site and a NotI site, respectively. The PCR product was cloned into MHC-pcDNA3 between the SpeI and NotI site in the MHC-pcDNA3 vector. The resulting vector was termed MHC-Calci*-pcDNA3. The sequence encoding the constitutively active calcineurin was verified by sequencing the construct using the following primers (forward 5'-CACCA-GAAATGACAGAC-3', (SEQ ID NO: 3) reverse 5'-AAAGGACAGTGGGAGTG-3' (SEQ ID NO: 4) situated in the vector, forward 5'-CACTCGCTACCTCTTCT-3' (SEQ ID NO: 5), reverse 5'-TCGTACTTCAACACTGC-3', (SEQ ID NO: 6) reverse 5'-AAATGTTCCTGAGTCTT-3' (SEQ ID NO: 7)). To allow selection of cardiomyocytes after differentiation from ES cells, the PIG vector (see WO02/051987), harboring an MHC promoter regulating the expression of a puromycin resistant gene-IRES-EGFP construct, was co-transfected with the MHCCalci* pcDNA3 vector. By addition of puromycin after differentiation, cardiomyocytes could be selected and identified by EGFP expression. The MHC-Calci*-pcDNA3 and PIG vectors were linearized with PvuI and SacI, respectively, and co-transfected into R1 ES cells (Nagy et al., Proc. Natl. Acad. Sci. 90 (1993), 8424-8428) by electroporation. As a negative control, a second R1 ES cell line was generated harboring the PIG construct only. Transfected cells were selected by neomycin resistance. In the case of cotransfecting of both MHC-Calci*-pcDNA3 and PIG vectors, PCR screening for identification of clones harboring both constructs was preformed using the following primers: forward 5'-CCTCACCCCCTGGCTTGT-3' (SEQ ID NO: 8) and reverse 5'-TTCCAGCCTGCCCTCCTT-3' (SEQ ID NO: 9), annealing temperature 57° C. for MHC-Calci*-pcDNA3 resulting in a product of 676 bp; forward 5-CAAGGACGACGGCAACTAC-3' (SEQ ID NO: 10) and reverse 5'-CGCTTCTCGTTGGGGTCT-3' (SEQ ID NO: 11), annealing temperature 57° C. for detection of PIG construct resulting in a fragment of 345 bp.

Figure 4:
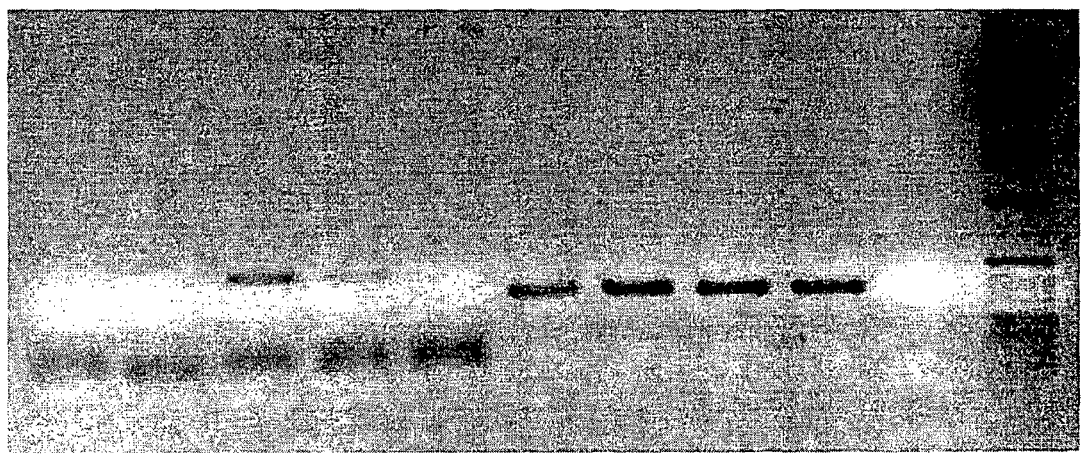
FIG. 4: Expression of constitutively active calcineurin leads to increased ANF mRNA levels in ES cell-derived cardiomyocytes.
Lanes 1, PIG clone (control), no serum starvation
Lanes 2, PIG clone (control), serum starved
Lanes 3, MHC-Calci*-PIG, no serum starvation
Lanes 4, MHC-Calci*-PIG, serum starved
Lanes 5, no cDNA
Left, Detection of ANF mRNA; right, detection of gapdh mRNA.

Differentiation of cells harboring both MHC-Calci*-pcDNA3 and PIG vectors was performed as follows: $1.5 \times 10^6$ undifferentiated ES cells/ml Iscove's medium (Invitrogen) with 15% FCS (Invitrogen) were cultivated in bacterial dishes (Greiner) during shaking (50 rpm, 37° C., % CO2) and after 6 h the cultures were diluted 1:10 and cultivated for additional 12 h to induce embryonic body (EB) formation. The EBs were then further diluted to a concentration 250 EBs/30 ml Iscove's medium with 15% FCS and were further cultivated under these conditions until day 9 of differentiation. RT-PCR was performed for identification of clones expressing the constitutively active calcineurin transcript using the following primers: forward 5'-CTGCTCCGACGATGAACT-3' (SEQ ID NO: 12) and reverse 5'-AAAGGACAGTGG-GAGTGG-3' (SEQ ID NO: 13), annealing temperature 57° C., product size 258 bp. Clones expressing the constitutively active Calcineurin transcript were selected for further analysis. A MHC-Calci*-PIG clone expressing constitutively active calcineurin transcripts and a control clone (harboring the PIG vector only) were differentiated as described in Example 1. On day 9 of differentiation, cardiomyocytes could be identified by fluorescent microscopy based on EGFP expression and the selection of cardiomyocytes was initiated by addition of 2 mg/ml puromycin to the medium. Selection was continued for 4 days and followed by cultivation in Iscove's medium with 15% FCS for another 5 days in the absence of puromycin. On day 18 of differentiation the cells were either starved in medium 199 (Invitrogen) without FCS or as control further cultured in Iscove's medium with 15% FCS for another 48h. RNA was prepared using the RNeasy mini kit (Qiagen) followed by RT-PCR analysis. Primers used for the ANF RT-PCR were, forward 5'-CTCCTTCTCCAT-CACCCTG-3' (SEQ ID NO: 14) and reverse 5'-TTTCCTC-CTTGGCTGTTATC-3' (SEQ ID NO: 15), annealing temperature 56° C., PCR resulting in a product of 468 bp. To control for input RNA and cDNA synthesis, gapdh cDNA was amplified by using the following primers: forward 5'-GTGT-TCCTACCCCCAATGTG-3' (SEQ ID NO: 16) and reverse 5'-CTTGCTCAGTGTCCTTGCTG-3' (SEQ ID NO: 17), annealing temperature 60° C., 349 bp PCR product. As an indication of a hypertrophic phenotype, an increase of the ANF RNA levels would be shown by RT-PCR analysis in clones expressing the constitutively active form of Calcineurin compared to control clones (FIG. 4). Increased ANF expression in cardiomyocytes is a hallmark of cardiomyocyte hypertrophy and has been reported to occur upon expression of a constitutively active calcineurin in vivo in transgenic mice (Molkentin et al., 1998) as well as in vitro in primary rat cardiomyocytes (De Windt et al., 2000). Thus, cardiomyocytes derived in vitro from ES cells transgenic for constitutively active calcineurin display features similar to conventional, previously described experimental systems of cardiomyocyte hypertrophy.

Example 3

Effects of Compounds on Hypertrophied Cardiomyocytes

In order to test if the hypertrophied cardiomyocytes obtained from ES cells as described in Example 1 represent a suitable tool for drug screening purposes, these cells were treated with compounds known to influence hypertrophic growth.

Puromycin resistant ES cell-derived cardiomyocytes were obtained as described in Example 1 and kept in suspension culture. The hypertrophic phenotype was induced by culturing the cells for 24 h in Medium 199 (Invitrogen), followed by treatment with 100 nM endothelin-1 (ET-1) or 100 μM phenylephrine (PE) and various test substances (Table 1) for 24 h in Medium 199. Subsequently, RNA was extracted using the RNeasy mini kit (Qiagen) followed by RT-PCR to analyse expression of ANF and BNP, two genes up-regulated in hypertrophied cardiomyocytes (see above). cDNA was synthezised, and ANF and BNP cDNAs were amplified by PCR (24 PCR cycles). Primers used for ANF amplification were as given in Example 2, and primers for BNP amplification were, forward 5'-CAGCTCTTGAAGGACCAAGG-3' (SEQ ID NO: 20) and reverse 5'-AGACCCAGGCAGAGTCAGAA-3' (SEQ ID NO: 21), annealing temperature 56° C., PCR resulting in a product of 242 bp. gapdh cDNA was amplified to control for input RNA and cDNA synthesis as described in Example 2. PCR products were separated by agarose gel electrophoresis and band intensity was analysed using the BioDocAnalyze system (Biometra).

Expression levels of ANF and BNP in samples that had been treated with ET-1 or PE, respectively, and with a test compound (Table 1) were determined relative to expression levels of the two genes in samples that had been stimulated by ET-1 or PE, respectively, but had not been treated with a test compound (these expression levels were set 100%).

Prazosin is a an alpha(1)-adrenergic antagonist. It was shown to block the hypertrophic response to alpha(1)-adrenergic stimulation in rat neonatal cardiomyocytes (Barron et al., Biochem J. 371 (PT 1) (2003), 71-79) and in adult rat ventricular myocytes (Xiao et al., J. Mol. Cell. Cardiol. 33 (2001), 779-787), and to prevent the phenotypic onset of cardiomyopathy in a hamster model (Sole and Liew, Am. J. Cardiol. 62 (1988), 20G-24G). On hypertrophy induction (measured by ANF induction) by treatment of cardiomyocytes by ET-1, prazosin had no effect (Barron et al., Biochem. J. 371 (PT 1) (2003), 71-79). These results are in agreement with the data shown for prazosin in Table 1, demonstrating inhibition of ANF and BNP induction upon PE treatment of ES cell derived cardiomyocytes, and no inhibition of ANF and BNP induction upon ET-1 stimulation of cardiomyocytes.

BQ-123 and BQ-788 are selective blockers of endothelin receptors A (ETA) and B (ETB), respectively. As expected, they inhibit ANF and BNP induction upon ET-1 stimulation, but not upon PE stimulation (Table 1).

Nifedipine and verapamil are $Ca^{2+}$ channel antagonists that have been used for treatment of hypertension and hypertrophic cardiomyopathy, among other disorders, in humans. Upon ET-1 stimulation of cardiomyocytes, both compounds inhibited BNP up-regulation, but not ANF up-regulation. Upon PE stimulation, ANF and BNP up-regulation was inhibited by nifedipine as well as by verapamil (Table 1). This is compatible with previous reports (Sole and Liew, Am. J. Cardiol. 62 (1988), 20G-24G; Pignier et al., Receptors Channels. 7 (2000), 173-187; Lubic et al., J. Mol. Cell. Cardiol. 27 (1995), 917-925).

The calcium/calmodulin-dependent protein phosphatase calcineurin has been implicated as an essential mediator of cardiac hypertrophy (Wilkins and Molkentin, Biochem. Biophys. Res. Commun. 322 (2004), 1178-1191). Calcineurin regulates the activity of a number of downstream targets, including the transcription factors NFAT, MEF2, and NF-kappaB, and the apoptotic factor Bad (Pu et al., Circ. Res. 92 (2003), 725-731). Cyclosporin A is an inhibitor of calcineurin and can prevent cardiac hypertrophy in cultured cardiomyocytes and in transgenic animal models (Zhang, Cardiovasc. Res. 53 (2002), 294-303). In ES cell-derived cardioyocytes, cyclosporin A inhibits the up-regulation of ANF and BNP expression upon treatment of cardiomyocytes by ET-1 as well as by PE (Table 1).

The protein kinase C inhibitor staurosporine was shown to block cardiomyocyte hypertrophic responses in cultured neonatal rat cardiac myocytes induced by ET-1 (Wu et al., Sheng Li Xue Bao. 150 (1998), 87-93) and by PE (Gaughan et al., Am. J. Physiol. 275 (1998), H577-H590). In accordance with these findings, staurosporine inhibited up-regulation of ANF and BNP expression in ES cell-derived cardiomyocytes stimulated by ET-1 or PE (Table 1).

In summary, the data given in Table 1 demonstrate that the compounds tested interfere with the induced hypertrophic phenotype of the ES cell-derived cardiomyocytes in a way that is consistent with published data on experimental animals with heart disease or on ex vivo isolated, hypertrophic cardiomyocytes. Therefore, these ES cell-derived cardiomyocytes that have been induced in vitro to obtain a hypertrophic phenotype are suitable for use in a drug discovery system that aims at drugs ameliorating pathologic hypertrophy of cardiomyocytes in heart disease.

TABLE 1

Interference of compounds with hypertrophy of ES cell-derived cardiomyocytes.

| Compound | Mode of action | Concentration | Stimulus | Induction of hypertrophic gene program | |
| --- | --- | --- | --- | --- | --- |
| | | | | ANF expression | BNP expression |
| Prazosin | $\alpha_1$-adrenergic antagonist | 10 μM | ET-1 | 100% (no effect) | 100% (no effect) |
| | | | PE | 40% | 40% |
| BQ123 | ETA receptor blocker | 1 μM | ET-1 | 50% | 60% |
| | | | PE | 100% (no effect) | 100% (no effect) |
| BQ788 | ETB receptor blocker | 1 μM | ET-1 | 70% | 70% |
| | | | PE | 100% (no effect) | 100% (no effect) |
| Nifedipine | $Ca^{2+}$ channel blocker | 100 nM | ET-1 | 100% (no effect) | 10% |
| | | | PE | 20% | 20% |
| Verapamil | $Ca^{2+}$ channel blocker | 1 μM | ET-1 | 100% (no effect) | 30% |
| | | | PE | 40% | 20% |

TABLE 1-continued

Interference of compounds with hypertrophy of ES cell-derived cardiomyocytes.

| Compound | Mode of action | Concentration | Stimulus | Induction of hypertrophic gene program | |
|---|---|---|---|---|---|
| | | | | ANF expression | BNP expression |
| Cyclosporin A | Calcineurin inhibitor | 1 µg/ml | ET-1 | 70% | 50% |
| | | | PE | 70% | 70% |
| Staurosporine | PKC inhibitor | 100 nM | ET-1 | 30% | 30% |
| | | | PE | 30% | 30% |

ES cell-derived cardiomyocytes were stimulated with either 100 nM endothelin-1 (ET-1) or 100 µM phenylephrine (PE) in the presence of the compounds indicated. After 24 hours expression of ANF and BNP mRNA was analyzed by RT-PCR. Expression levels of ANF and BNP were determined relative to expression levels of the two genes in control samples that had been stimulated by ET-1 or PE but had not been treated with a test compound (these expression levels were set 100%).

It will be recognized that the compositions and procedures provided in the description can be effectively modified by those skilled in the art without departing from the spirit of the invention embodied in the claims that follow.

The invention claimed is:

1. An in vitro method for screening and identifying a candidate substance capable of ameliorating hypertrophic cardiomyopathy comprising:
   (a) differentiating a pluripotent stem cell to a cardiomyocyte in vitro;
   (b) inducing the cardiomyocyte to display a first cardiac hypertrophic phenotype;
      (i) wherein the inducing results in the cardiomyocyte having an increased size, protein production and/or sarcomeric assembly relative to the same cardiomyocyte prior to the inducing in step (b); and/or
      (ii) wherein the inducing results in the cardiomyocyte expressing atrial natriuretic factor (ANF) and/or brain natriuretic protein (BNP) genes or their products in an amount greater than the cardiomyocyte prior to the inducing in step (b);
   (c) contacting a test sample comprising the in vitro differentiated cardiomyocyte with a substance to be tested prior, during or after said cardiomyocyte is induced to display the cardiac hypertrophic phenotype;
   (d) measuring a second cardiac hypertrophic phenotype in the cardiomyocyte of step (c);
   (e) comparing the measurement obtained in step (d) to that of a cardiomyocyte not subjected to the substance to be tested;
   wherein the candidate substance is identified on the basis of whether the measurement of the second cardiac hypertrophic phenotype in the cardiomyocyte of step (d) is consistent with a reduction in hypertrophic cardiomyopathy.

2. The method of claim 1, wherein the second cardiac hypertrophic phenotype is:
   a) expression of a gene or activity of a gene product selected from the group consisting of an atrial natriuretic factor (ANF) gene, a b-type natriuretic peptide (BNP) gene, a β-myosin heavy chain gene, an α-skeletal actin gene, c-FOS, e-JUN, c-MYC, early growth response genes, heat shock protein 70, alpha-myosin heavy chain, collagen III, preproendothelin-1, myosin light chain 2, $Na^+/H^+$ exchanger, cardiac alpha-actin, $Na^+/Ca^{2+}$ exchanger, phosphatidylinositol-3 receptor, angiotensin-converting enzyme, collagen I, collagen XV, sarcoplasmic reticulum Ca-ATPase-2 alpha, beta-adrenoreceptor, protein kinase C, and phospholamban; and/or
   b) cell size, protein production and/or sarcomeric assembly.

3. The method of claim 1, wherein said contacting further includes contacting said test sample with at least one second candidate substance in the presence of said first candidate substance.

4. The method of claim 1, wherein more than one second cardiac hypertrophic phenotype is measured in step (d).

5. The method of claim 4, wherein the second cardiac hypertrophic phenotypes include the expression of the genes atrial natriuretic factor and/or brain natriuretic peptide or activity of their gene products.

6. The method of claim 1 wherein the first cardiac hypertrophic phenotype is induced by a nucleotide sequence.

7. The method of claim 6 wherein the nucleotide sequence comprises a regulatory sequence of a gene expressed in cardiac tissue.

8. The method of claim 7 wherein the nucleotide sequence encodes a calcineurin protein.

9. The method of claim 1 wherein the first hypertrophic phenotype is induced by a physiological agent selected from the group consisting of endothelins, phenylephrine, alpha-1-adrenergic agonists angiotensin-II and a nucleotide sequence comprising a regulatory sequence of a gene expressed in cardiac tissue; or induced by mechanical stimulus.

10. The method of claim 1 wherein the inducing results in the cardiomyocyte having an increased size, protein production and/or sarcomeric assembly relative to the cardiomyocyte prior to the inducing in step (b).

11. The method of claim 1 wherein the inducing results in the cardiomyocyte expressing atrial natriuretic factor (ANF) and/or brain natriuretic protein (BNP) genes or their gene products in an amount greater than the cardiomyocyte prior to the inducing in step (b).

12. The method of claim 1 wherein a control cardiac hypertrophic phenotype is measured before step (b).

13. The method of claim 12 wherein the control cardiac hypertrophic phenotype is compared to the measurement obtained in step (d).

14. The method of claim 1 wherein said pluripotent cell is an embryonic stem (ES) cell.

15. The method of claim 1 wherein the said cardiomyocyte comprises a selectable marker gene operably linked to a cell type specific regulatory sequence.

16. The method of claim 15, wherein said selectable marker gene confers resistance to puromycin.

17. The method of claim 15, wherein said cardiomyocyte comprises a reporter gene operably linked to a cell type specific regulatory sequence.

18. The method of claim 17, wherein said cell type specific regulatory sequence of the reporter gene is substantially the same as said cell type specific regulatory sequence of the marker gene.

19. The method of claim 18, wherein said selectable marker gene and said reporter gene are contained on the same recombinant nucleic acid molecule.

20. The method of claim 15, wherein said cell type specific regulatory sequence is atrial and/or ventricular specific.

21. The method of claim 15, wherein said cell type specific regulatory sequence is a cardiac specific promoter selected from the group consisting of αMHC promoter, MLC2v promoter, MLCIa promoter, MLC2a promoter and βMHC promoter.

22. The method of claim 1, wherein said cardiomyocyte is present in a cell aggregate.

23. The method of claim 8, wherein the calcineurin protein is a constitutively active calcineurin protein.

24. The method of claim 1 wherein the second cardiac hypertrophic phenotype is selected from the group consisting of a rate of protein synthesis, cell size and sarcomeric organization.

25. The method of claim 1 wherein the second cardiac hypertrophic phenotype is selected from the group consisting of actin/myosin filament organization, activation of gene expression pattern characteristic of cardiomyopathic cells, and/or activation of genes expressed during early embryonic development.

26. The method of claim 6 wherein the nucleotide sequence encodes a protein selected from the group consisting of mutant and wild type versions of the following: troponin, myosin heavy chain, calcineurin, calmodulin, protein kinase C, phospholamban, beta-myosin heavy chain, regulatory myosin light chain, alpha-tropomyosin and calcium calmodulin dependent kinase IV (CaMKIV).

27. The method of claim 1 wherein the inducing results in the cardiomyocyte expressing atrial natriuretic factor (ANF) gene and/or protein in an amount greater than the cardiomyocyte prior to the inducing in step (b).

28. The method of claim 1 wherein the inducing results in the cardiomyocyte expressing brain natriuretic protein (BNP) gene and/or protein in an amount greater than the cardiomyocyte prior to the inducing in step (b).

29. The method of claim 1 wherein the first cardiac hypertrophic phenotype and the second cardiac hypertrophic phenotype are the same.

30. The method of claim 1 wherein the first cardiac hypertrophic phenotype and the second cardiac hypertrophic phenotype are different.

* * * * *

SEQUENCE LISTING

```
<160> NUMBER OF SEQ ID NOS: 21

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggactagtcc agccaccatg tccgagccca aggc                               34

<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ataagaatgc ggccgctaaa ctattcagtt tctgatgact tccttccgg               49

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caccagaaat gacagac                                                 17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaaggacagt gggagtg                                                 17
```

```
<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cactcgctac ctcttct                                                   17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcgtacttca acactgc                                                   17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaatgttcct gagtctt                                                   17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctcaccccc tggcttgt                                                  18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttccagcctg ccctcctt                                                  18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caaggacgac ggcaactac                                                 19
```

-continued

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcttctcgt tggggtct                                                 18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgctccgac gatgaact                                                 18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaaggacagt gggagtgg                                                 18

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctccttctcc atcaccctg                                                19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttcctcctt ggctgttatc                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtgttcctac ccccaatgtg                                               20

<210> SEQ ID NO 17
<211> LENGTH: 20

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cttgctcagt gtccttgctg                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagctcttga aggaccaagg                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agacccaggc agagtcagaa                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagctcttga aggaccaagg                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agacccaggc agagtcagaa                                               20
```